United States Patent
Linhardt et al.

(10) Patent No.: US 10,603,854 B2
(45) Date of Patent: Mar. 31, 2020

(54) METHODS AND APPARATUS FOR POSITIONING A STRUCTURE ON A POLYMER LAYER

(71) Applicant: Verily Life Sciences LLC, Mountain View, CA (US)

(72) Inventors: Jeffrey George Linhardt, Pleasanton, CA (US); Daniel Patrick Barrows, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 254 days.

(21) Appl. No.: 15/701,414

(22) Filed: Sep. 11, 2017

(65) Prior Publication Data

US 2018/0009181 A1 Jan. 11, 2018

Related U.S. Application Data

(62) Division of application No. 14/143,842, filed on Dec. 30, 2013, now Pat. No. 9,782,942.

(51) Int. Cl.
*B29D 11/00* (2006.01)
*B29C 31/00* (2006.01)
(Continued)

(52) U.S. Cl.
CPC ...... *B29D 11/00807* (2013.01); *B29C 31/008* (2013.01); *B29C 65/483* (2013.01);
(Continued)

(58) Field of Classification Search
CPC .......... B29D 11/00807; B29C 66/5326; B29C 66/81457; B29C 66/8161;
(Continued)

(56) References Cited

U.S. PATENT DOCUMENTS 3,971,841 A    7/1976   Rubinstein
4,029,911 A    6/1977   Albinger
(Continued)

FOREIGN PATENT DOCUMENTS

EP    0592768    11/1997
GB    620196    3/1949
(Continued)

OTHER PUBLICATIONS

International Search Report and Written Opinion prepared by the Korean Patent Office in international patent application serial No. PCT/US2014/072480 dated Mar. 31, 2015.

*Primary Examiner* — Mathieu D Vargot
(74) *Attorney, Agent, or Firm* — McDonnell Boehnen Hulbert & Berghoff LLP

(57) ABSTRACT

Methods and apparatus for positioning a structure on a polymer layer are described. A method may involve forming a first polymer layer. The method may further involve positioning, by an apparatus, a structure on the first polymer layer, where the apparatus comprises a rod having a first end that supports the structure as the structure is being positioned and a plunger located around the first end of the rod that presses the structure onto the first polymer layer as the structure is being positioned. And the method may involve forming a second polymer layer over the first polymer layer and the structure, where the first polymer layer defines a first side of a body-mountable device and the second polymer layer defines a second side of the body-mountable device opposite the first side.

15 Claims, 15 Drawing Sheets

(51) Int. Cl.
*B29C 65/00* (2006.01)
*B29C 65/48* (2006.01)
*B29C 65/78* (2006.01)
*A61B 3/10* (2006.01)
*G02C 7/04* (2006.01)
*B29L 11/00* (2006.01)
*B29C 65/52* (2006.01)
*B29C 65/02* (2006.01)

(52) U.S. Cl.
CPC ...... *B29C 65/7811* (2013.01); *B29C 66/1122* (2013.01); *B29C 66/5324* (2013.01); *B29C 66/5326* (2013.01); *B29C 66/8161* (2013.01); *B29C 66/81457* (2013.01); *B29C 66/8322* (2013.01); *B29C 66/92451* (2013.01); *A61B 3/101* (2013.01); *B29C 65/02* (2013.01); *B29C 65/4835* (2013.01); *B29C 65/4845* (2013.01); *B29C 65/522* (2013.01); *B29C 65/526* (2013.01); *B29C 65/7814* (2013.01); *B29C 65/7844* (2013.01); *B29C 66/8122* (2013.01); *B29L 2011/0041* (2013.01); *G02C 7/04* (2013.01)

(58) Field of Classification Search
CPC ............ B29C 66/92451; B29C 65/483; B29C 65/7811; B29C 31/008
See application file for complete search history.

(56) References Cited

U.S. PATENT DOCUMENTS

| | | |
|---|---|---|
| 5,232,637 A | 8/1993 | Dasher et al. |
| 8,038,912 B2 | 10/2011 | Beebe et al. |
| 9,782,942 B2 | 10/2017 | Linhardt et al. |
| 2002/0180106 A1 | 12/2002 | Ogata et al. |
| 2009/0070983 A1 | 3/2009 | Stumpf et al. |
| 2010/0072643 A1 | 3/2010 | Pugh et al. |
| 2010/0078838 A1 | 4/2010 | Pugh et al. |
| 2010/0110372 A1 | 5/2010 | Pugh et al. |
| 2012/0234493 A1 | 9/2012 | Pugh et al. |
| 2013/0225968 A1 | 8/2013 | Auvray et al. |

FOREIGN PATENT DOCUMENTS

| | | |
|---|---|---|
| JP | S62 65276 | 3/1987 |
| SU | 1796816 A1 * | 2/1993 |
| WO | WO2004/096529 | 11/2004 |

* cited by examiner

METHODS AND APPARATUS FOR POSITIONING A STRUCTURE ON A POLYMER LAYER

CROSS-REFERENCE TO RELATED APPLICATION

This application is a division of application Ser. No. 14/143,842, filed Dec. 30, 2013, now U.S. Pat. No. 9,782,942 which is incorporated herein by reference.

BACKGROUND

Unless otherwise indicated herein, the materials described in this section are not prior art to the claims in this application and are not admitted to be prior art by inclusion in this section.

A body-mountable device may be configured to monitor health-related information based on at least one analyte detected in a fluid of a user wearing the body-mountable device. For example, the body-mountable device may comprise an eye-mountable device that may be in the form of a contact lens that includes a sensor configured to detect the at least one analyte (e.g., glucose) in a tear film of a user wearing the eye-mountable device. The body-mountable device may also be configured to monitor various other types of health-related information.

SUMMARY

In one aspect, the present disclosure provides a method. The method involves: forming a first polymer layer; positioning, by an apparatus, a structure on the first polymer layer, where the apparatus comprises a rod having a first end that supports the structure as the structure is being positioned and a plunger located around the first end of the rod that presses the structure onto the first polymer layer as the structure is being positioned; and forming a second polymer layer over the first polymer layer and the structure, where the first polymer layer defines a first side of a body-mountable device and the second polymer layer defines a second side of the body-mountable device opposite the first side.

In another aspect, the present disclosure provides an apparatus for placing a structure on a polymer layer. The apparatus includes: a rod having a first end that is configured to support the structure as the structure is being positioned on the polymer layer; and a plunger located around the first end of the rod, where the plunger is configured to press the structure onto the polymer layer as the structure is being positioned on the polymer layer.

In another aspect, the present disclosure provides a system. The system includes: means for forming a first polymer layer; means for positioning a structure on the first polymer layer; and means for forming a second polymer layer over the first polymer layer and the structure, where the first polymer layer defines a first side of a body-mountable device and the second polymer layer defines a second side of the body-mountable device opposite the first side.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 3c-2 is an illustration of an example structure, according to an example embodiment.

DETAILED DESCRIPTION

Figure 1:
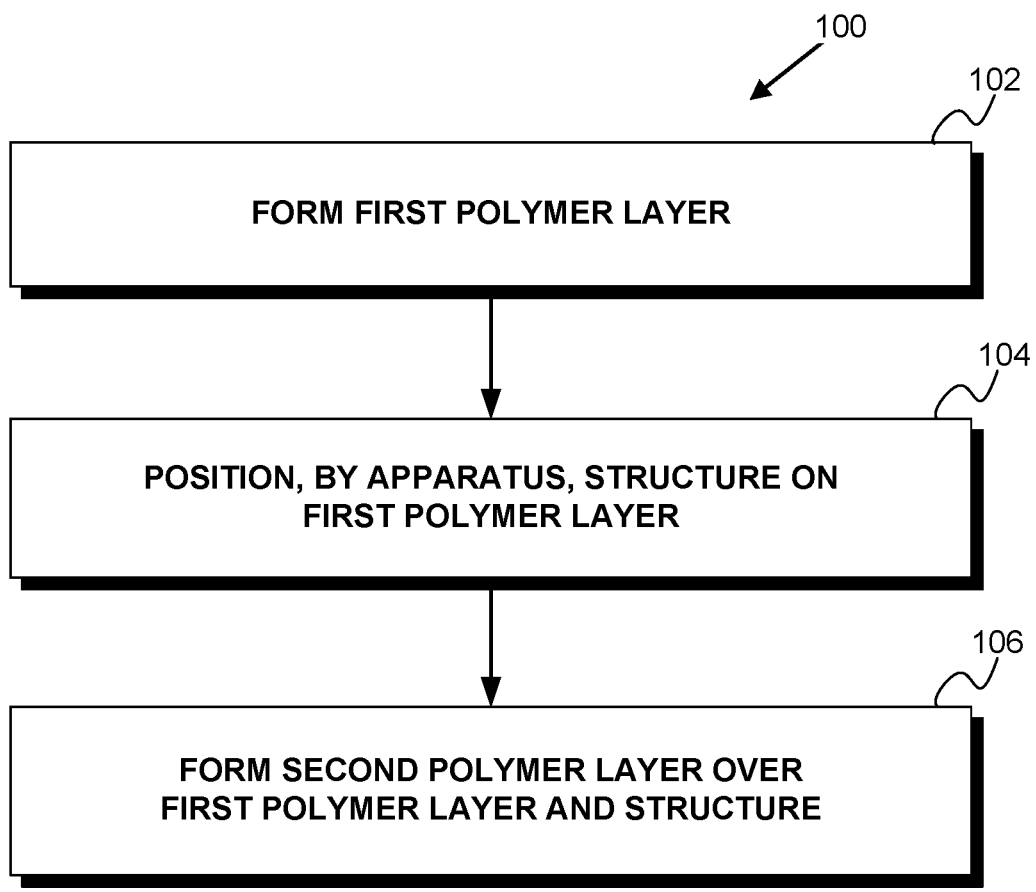
FIG. 1 is a flow chart illustrating a method according to an example embodiment.

The following detailed description describes various features and functions of the disclosed methods, apparatus, and systems with reference to the accompanying figures. In the figures, similar symbols typically identify similar components, unless context dictates otherwise. The illustrative method, apparatus, and system embodiments described herein are not meant to be limiting. It will be readily understood that certain aspects of the disclosed methods, apparatus, and systems can be arranged and combined in a wide variety of different configurations, all of which are contemplated herein.

I. Introduction

A body-mountable device may be configured to monitor health-related information based on at least one analyte detected in a fluid of a user wearing the body-mountable device. Such a body-mountable device may include a structure located between a first polymer layer and second polymer layer. Further, the structure may include one or more components, such as a sensor that is configured to detect the at least one analyte.

Such a body-mountable device may be formed (e.g., fabricated) by positioning, by an apparatus, the structure on the first polymer layer. The apparatus may include a rod having a first end that supports the structure as the structure is being positioned and a plunger located around the first end of the rod that presses the structure onto the first polymer layer as the structure is being positioned.

Beneficially, embodiments described herein may help to improve positioning of the structure on the first polymer layer. For instance, fabrication of body-mountable devices in accordance with an example embodiment may allow for positioning the structure at a predetermined orientation on a polymer layer, such as centered on the first polymer layer. With this arrangement, distortion of the first and second polymer layers and/or at least one component of the structure, such as an antenna, may be reduced. And when the body-mountable comprises an eye-mountable device, positioning the structure centered on the first polymer layer may improve the wearer's line of sight.

In addition, fabrication of body-mountable devices in accordance with an example embodiment may allow for positioning the structure at a predetermined location on a polymer layer, such as at a center of the first polymer layer.

As used throughout this disclosure, the anterior side of the body-mountable device refers to an outward-facing side of the body-mountable device, whereas the posterior side of the body-mountable device refers to an inward-facing side of the body-mountable device. In particular, when the body-mountable device comprises an eye-mountable device and the eye-mountable device is mounted on an eye of the user, the anterior side corresponds to a side of the eye-mountable device that is facing outward and thus not touching the eye of the user. Further, when the eye-mountable device is mounted on an eye of the user, the posterior side corresponds to a side of the eye-mountable device that is facing inward and thus touching the eye of the user.

II. Example Methods

Example methods for forming a body-mountable device are disclosed. FIG. 1 is a flow chart illustrating a method 100 according to an example embodiment. More specifically, as shown by block 102, the method 100 may involve forming a first polymer layer. Further, as shown by block 104, the method 100 may involve positioning, by an apparatus, a structure on the first polymer layer, wherein the apparatus comprises a rod having a first end that supports the structure as the structure is being positioned and a plunger located around the first end of the rod that presses the structure onto the first polymer layer as the structure is being positioned. Further still, as shown by block 106, the method 100 may involve forming a second polymer layer over the first polymer layer and the structure, wherein the first polymer layer defines a first side of the body-mountable device and the second polymer layer defines a second side of the body-mountable device opposite the first side.

Figure 2:
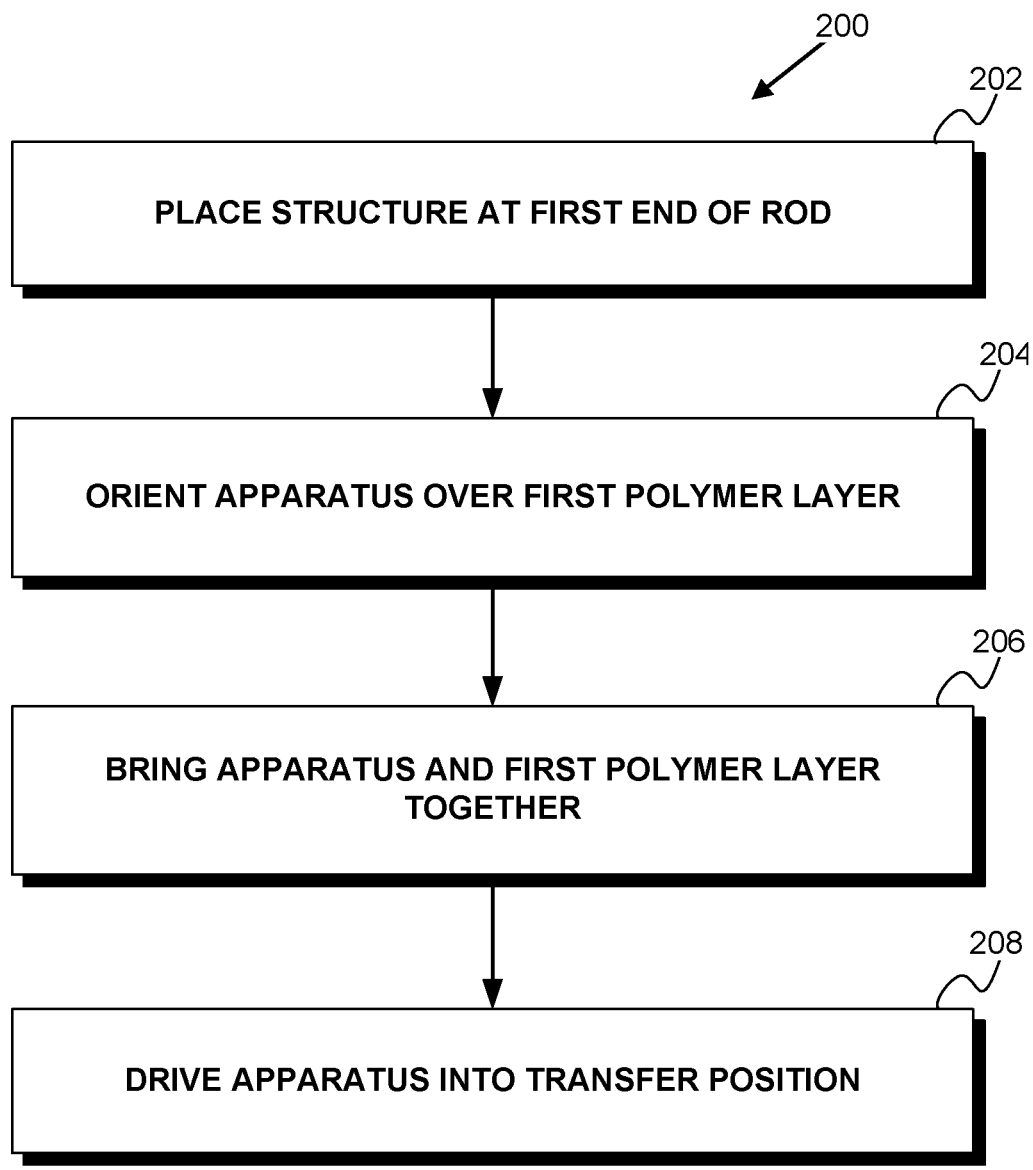
FIG. 2 is a flow chart illustrating another method according to an example embodiment.

In addition, FIG. 2 is a flow chart illustrating another method 200 according to an example embodiment. The method 200 may be performed in connection with block 104 of method 100. More specifically, as shown by block 202, the method 200 may involve placing the structure at a first end of the rod. Further, as shown by block 204, the method 200 may involve orienting the apparatus over the first polymer layer, wherein the orienting of the apparatus over the first polymer layer positions a portion of the structure directly above a predetermined location on the first polymer layer. Further still, as shown by block 206, the method 200 may involve bringing the apparatus and the first polymer layer together, such that the first end of the rod contacts the first polymer layer; and driving the apparatus into a transfer position, wherein in the transfer position: (i) the plunger presses the structure onto the first polymer layer and (ii) the rod retracts into the housing.

For purposes of illustration, the method 100 and the method 200 are described below as being carried out by a fabrication device that utilizes various methods and/or processes for fabricating body-mountable devices. It should be understood, however, that the method 100 and/or the method 200 may be carried out by a fabrication device that utilizes other methods and/or processes for fabricating body-mountable devices.

Moreover, for purposes of illustration, the method 100 and the method 200 are described below in a scenario where a body-mountable device comprises an eye-mountable device. It should be understood, however, that the method 100 and/or the method 200 may involve scenarios where the body-mountable device comprises other mountable devices that are mounted on or in other portions of the human body. For example, the body-mountable device may comprise a tooth-mountable device and/or a skin-mountable device.

Method 100 and method 200 will now be described in greater detail below with reference to FIGS. 3a-3g. It is noted that relative dimensions in FIGS. 3a-3g are not necessarily to scale, but have been rendered for purposes of explanation only in describing the method 100 and the method 200.

A. Forming a First Polymer Layer

Figure 3A:
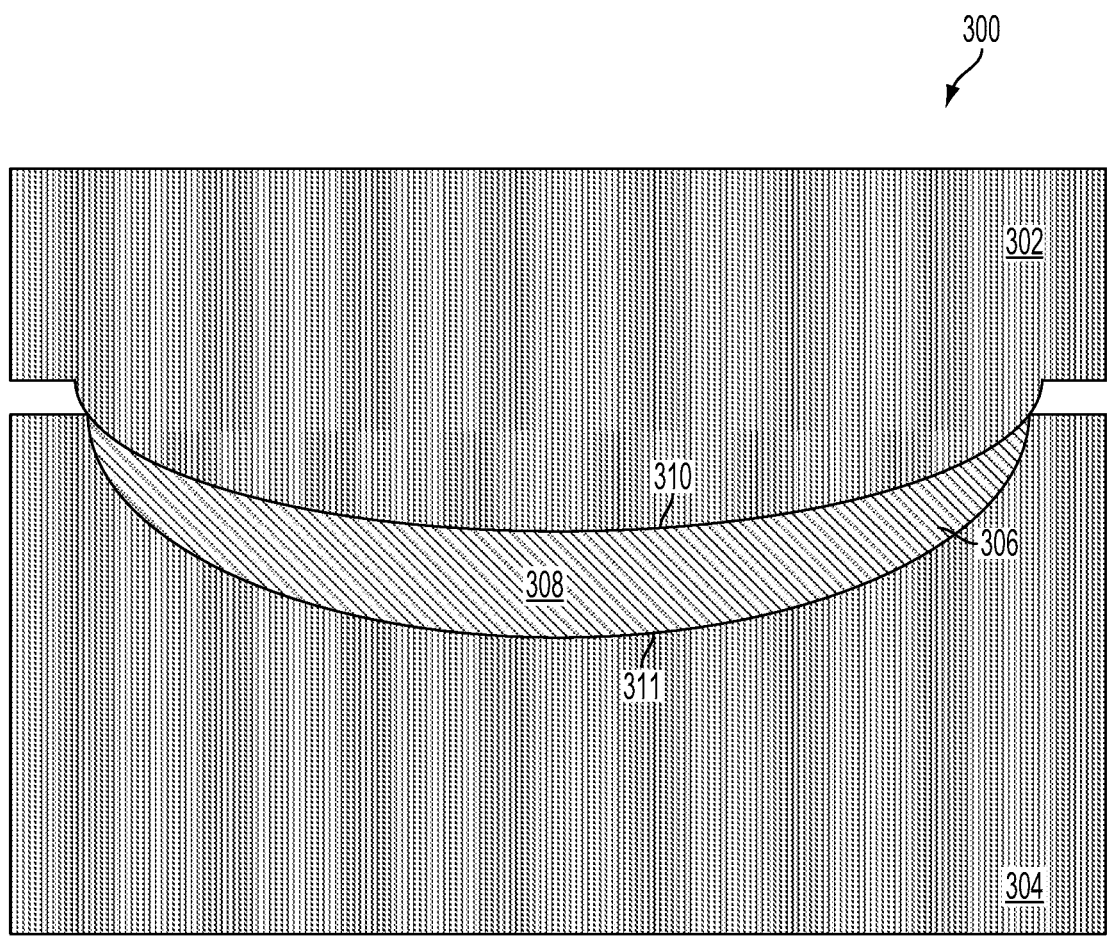
FIG. 3a is an illustration of formation of a first polymer layer, according to an example embodiment.

As mentioned above, at block 102, the fabrication device may be used to form a first polymer layer. The fabrication device may include molding pieces, such as molding pieces that are suitable for cast molding. FIG. 3a illustrates a fabrication device 300 that includes molding pieces that may be used to form the first polymer layer. In particular, FIG. 3a illustrates the fabrication device 300 including a first molding piece 302 and a second molding piece 304. The first molding piece 302 and the second molding piece 304 may define a first cavity. A polymer material 306 may be provided on a surface of the second molding piece 304, and the polymer material 306 may be compressed into a first polymer layer 308 by the first molding piece 302. In an example, the polymer material 306 may be provided on the surface of the second molding piece 304 by filling the second molding piece 304 with the polymer material 306.

After the polymer material 306 is compressed into the first polymer layer 308, the fabrication device 300 may cure the first polymer layer 308. In an example, the polymer material 306 can be a light-curable polymer material, and the fabrication device 300 may be configured to cure the light-curable polymer material using light, such as ultraviolet light or visible light. In an example, the first polymer layer 308 may be cured to a partially-cured state. In such an example, this may involve curing the material to a partially-cured state that is approximately 50-75% of a fully cured state. Other partially-cured states are possible as well. Beneficially, by partially curing the first polymer layer 308 to a partially-cured state, the first polymer layer 308 may have a tackiness that facilitates adhesion thereto. With this arrangement, the tackiness may facilitate a structure placed on the first polymer layer 308 remaining securely fixed in a given location during subsequent formation steps.

The tackiness exhibited by the partially-cured first polymer layer 308 may be different for different polymers. Accordingly, the fabrication device 300 may be configured to cure different polymer materials differently than other polymer materials (e.g., a first polymer material may be cured more than a second polymer material). Further, in addition to light curing, other methods of curing are possible as well, such as chemical additives and/or heat. For instance, the first polymer material may be cured at a certain temperature, such as between 100 degrees Celsius (C) to 150 degrees C. Yet still further, in other example embodiments, the first polymer layer 308 may be completely cured. Alternatively, the fabrication device 300 may bypass curing the first polymer layer 308 at this stage.

The first molding piece 302 and the second molding piece 304 may be configured to achieve a given desired thickness of the first polymer layer 308. For instance, in an example, the first polymer layer 308 can have a thickness of less than 150 micrometers. In an example embodiment, the first molding piece 302 and the second molding piece 304 can be designed so as to allow for a layer having less than a 150 micrometer thickness between the two cavities. As such, when the first molding piece 302 and the second molding piece 304 are pressed together during the formation of the first polymer layer 308, the resulting polymer layer 308 will have a thickness of less than 150 micrometers.

In an example, the thickness of the first polymer layer 308 can be selected based on a particular analyte or analytes an eye-mountable device is configured to detect. For example, an optimal thickness for a first analyte may be 10 micrometers, while an optimal thickness for a second analyte may be 25 micrometers. Other examples are possible as well.

In an example, the polymer material 306 can be any material that can form an eye-compatible polymer layer. For example, the polymer material 306 may be a formulation containing polymerizable monomers, such as hydrogels, silicone hydrogels, silicone elastomers, and rigid gas permeable materials. Further, the polymer material 306 may form a transparent or substantially transparent polymer layer. As such, the use of the polymer material 306 may result in an eye-mountable device through which the wearer can see when mounted on the wearer's eye. In an example, the polymer material 306 can be a hydrogel material, such as silicone hydrogel. As known in the art, hydrogel materials are commonly used in contact-lens technology and are well-suited for eye-mountable devices. Other materials are possible as well.

In an example, the first molding piece 302 and/or the second molding piece 304 can be configured so as to allow sufficient pinch off to provide for suitable edges for an eye-mountable device.

Further, in an example, the first molding piece 302 and the second molding piece 304 may be transparent, such that the polymer material 306 may be visible during formation of the first polymer layer 308. Such an arrangement may assist in orienting the first molding piece 302 and/or the second molding piece 304.

The first polymer layer 308 defines a posterior side (or a first side) 310 of an eye-mountable device. That is, the first polymer layer 308 defines an outer edge of the eye-mountable device. When mounted on an eye of a user, the posterior side 310 of the eye-mountable device defined by the first polymer layer 308 corresponds to a side of the device touching the eye of the user. The first molding piece 302 may be shaped so as to define a shape of the posterior side 310. For example, a curvature of the posterior side 310 may be defined by the first molding piece 302. The first polymer layer 308 may also have a side 311 opposite the posterior side 310. The second molding piece 304 may be shaped so as to define a shape of the side 311. For example, a curvature of the side 311 may be defined by the second molding piece 304.

As mentioned above, although FIG. 3a illustrates forming the first polymer layer 308 through cast molding, other methods for forming the first polymer layer 308 are possible as well. For example, the first polymer layer 308 may be formed via injection molding. In injection molding, rather than polymer material being compressed between molding pieces, molding material may be heated and injected or otherwise forced into a molding piece or pieces. The injected molding material may then cool and harden to the configuration of the molding piece or pieces.

As another example, the first polymer layer 308 may be formed via spin casting. Through spin-casting techniques, the fabrication device 300 may form a first polymer layer of a precise thickness. In an example, a spin-casting mold may be spun along its central access at a set speed, and the polymer may be introduced to the mold as the mold is spinning in order to form a first polymer layer. The final thickness of the first polymer layer may be influenced by various factors, including but not limited to the spin-casting mold, the amount of polymer introduced to the spin-casting mold, properties of the polymer such as viscosity, and/or the speed at which the spin-casting mold is rotated. These factors may be varied in order to result in a first polymer layer of a well-defined thickness.

B. Positioning, by an Apparatus, a Structure on the First Polymer Layer

Figure 3B:
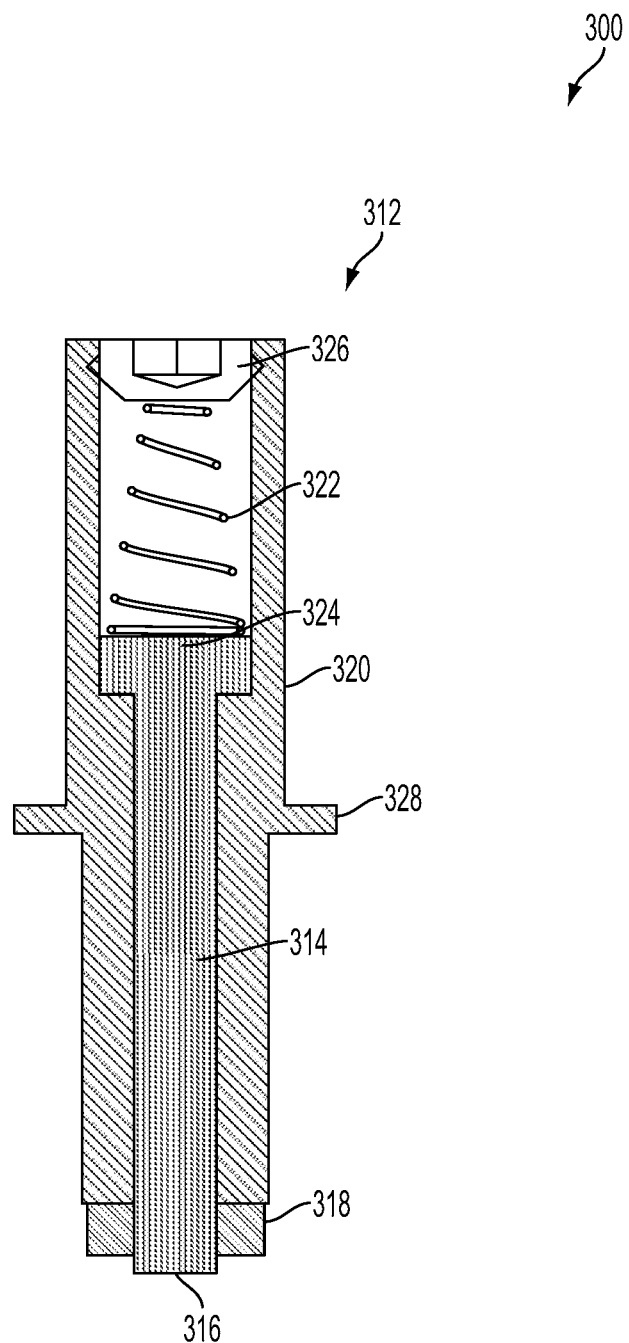
FIG. 3b is an illustration of an apparatus, according to an example embodiment.

As mentioned above, at block 104, a structure may be positioned on the first polymer layer by an apparatus. FIGS. 3b-3f illustrate fabrication device 300 including equipment that may be used to position a structure on a polymer layer. In particular, FIG. 3b illustrates an apparatus 312 that may be used to position a structure on the first polymer layer 308, such as a structure 330 (as illustrated in FIGS. 3c-3f). In some embodiments, the apparatus of the method 100 and/or the method 200 may take the form of or be similar in form to the apparatus 312.

Figures 2, 3C:
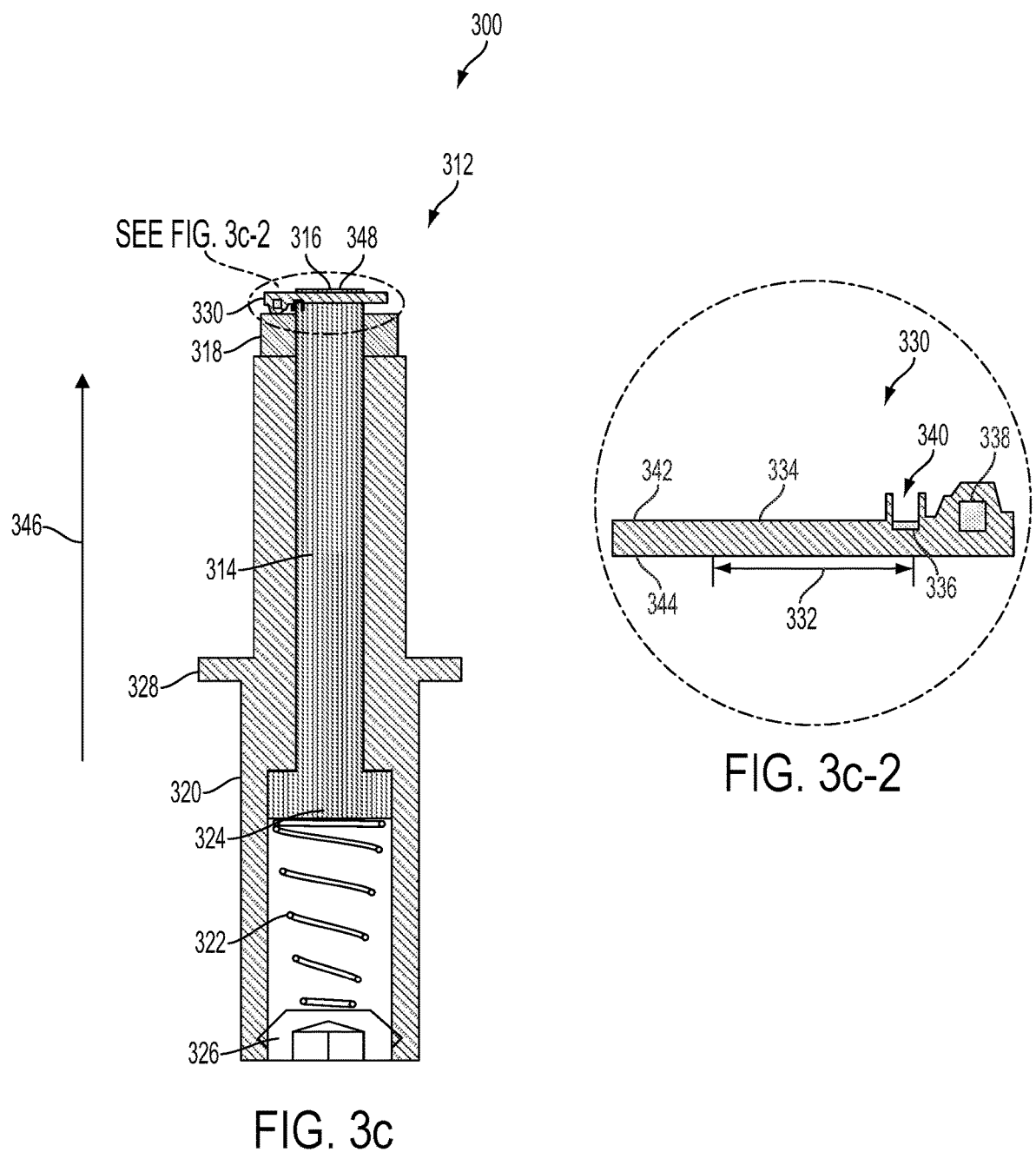
FIG. 3c is an illustration of placing the structure at a first end of a rod, according to an example embodiment.
Figure 3D:
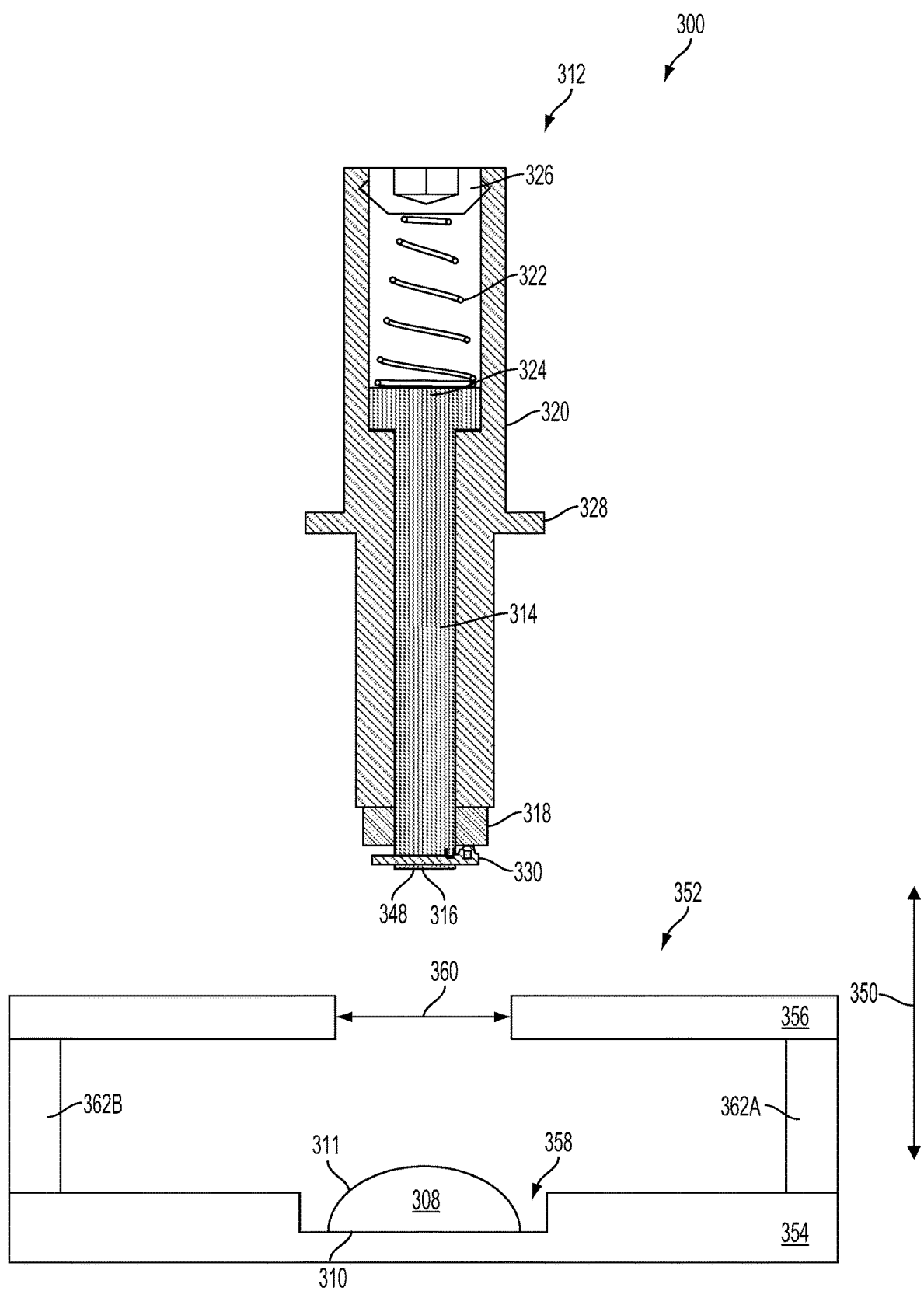
FIG. 3d is an illustration of orienting the apparatus over the first polymer layer, according to an example embodiment.
Figure 3E:
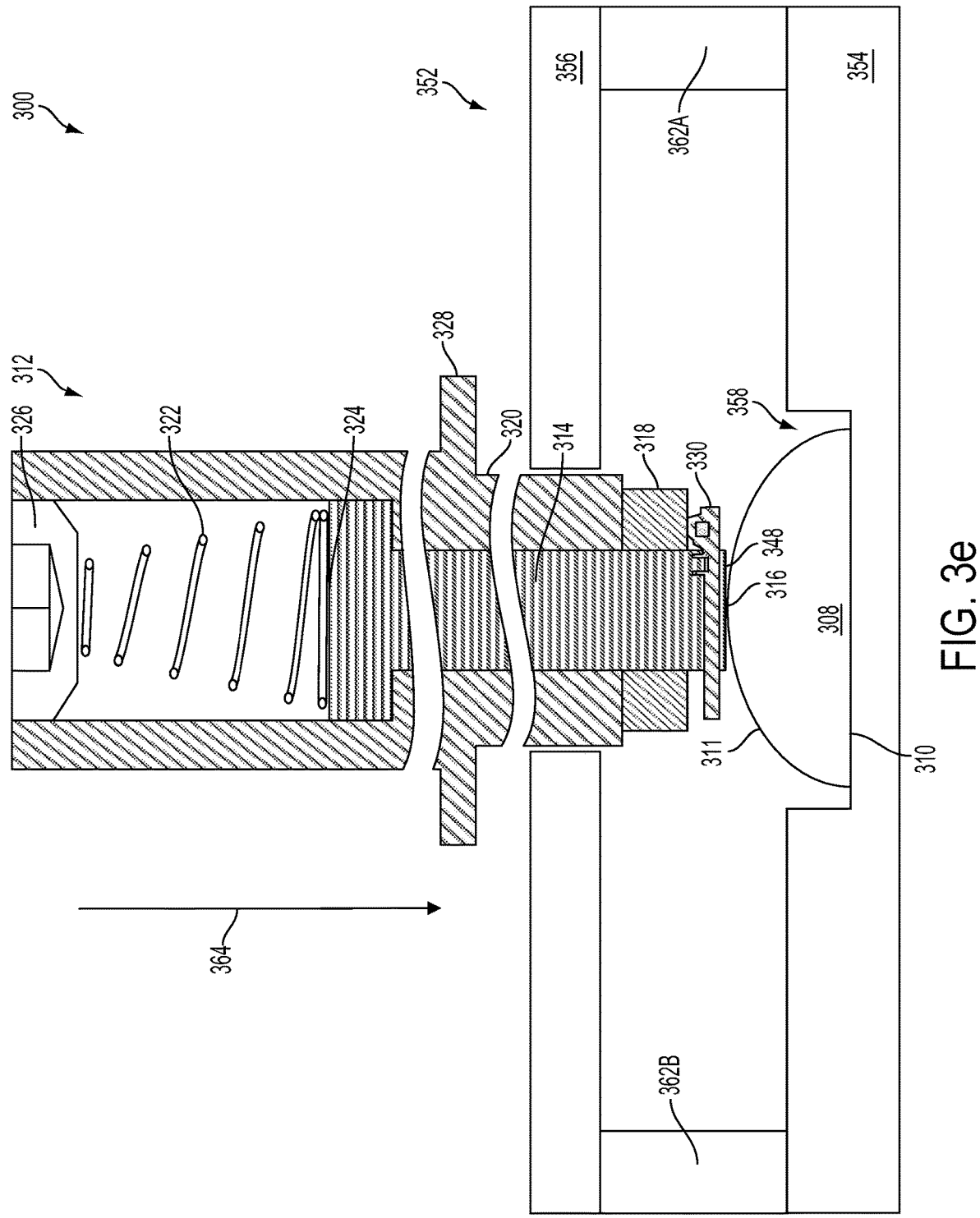
FIG. 3e is an illustration of bringing the apparatus and the first polymer layer together, according to an example embodiment.
Figure 3F:
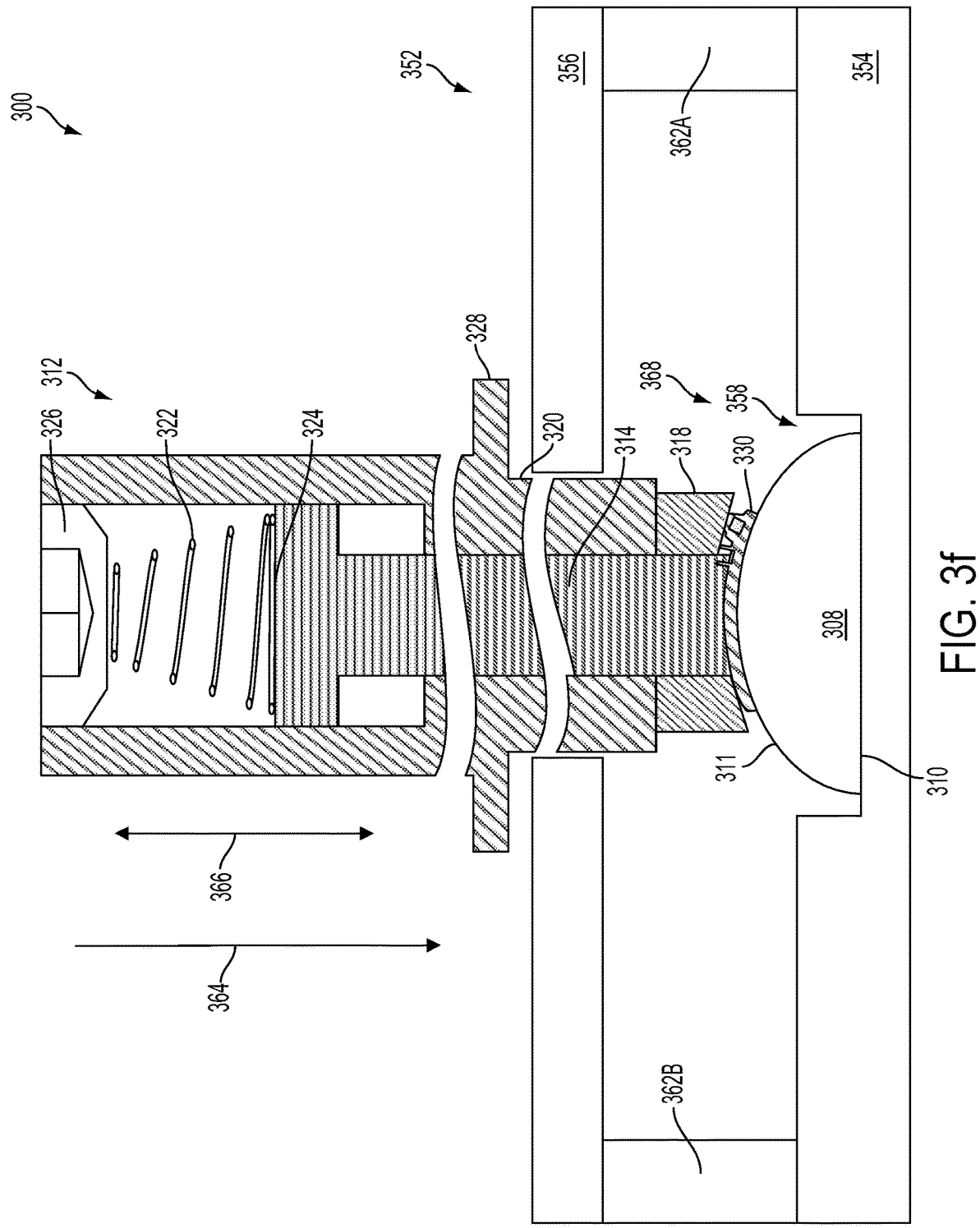
FIG. 3f is an illustration of driving the apparatus into a transfer position, according to an example embodiment.

As shown in FIG. 3b, the apparatus 312 includes a rod 314 having a first end 316 that supports the structure 330 as the structure 330 is being positioned (as illustrated in FIGS. 3c-3f) and a plunger 318 located around the first end 316 of the rod 314 that presses the structure 330 onto the first polymer layer 308 as the structure 330 is being positioned (as illustrated in FIG. 3f). In addition, as shown in FIG. 3b, the first end 316 of the rod 314 may extend beyond the plunger 318.

Further, as shown in FIG. 3b, the apparatus 312 may further include a housing 320 and a spring 322, and the rod 314 may further include a second end 324. The spring 322 may be connected to the second end 324 of the rod 314 and may be configured to retract the rod 314 into the housing 320 during the positioning of the structure 330 (as illustrated in FIG. 3f). Further, the spring 322 may be connected to the housing 320. In the illustrated example, the spring 322 may be connected to the housing 320 via a set screw 326. In addition, as shown in FIG. 3b, the housing 320 may further include a flange 328.

The rod 314 may take various different forms in various different embodiments. For instance, in some embodiments, the rod 314 may include a complaint material. As examples, the rod 314 may include a polymer material, such as polyetherimide, silicone, polyethylene terephthalate (PET), polypropylene, polyurethane, and silicone rubber. And in at least one such embodiment, the rod 314 may be Ultem® sold by SABIC.

Moreover, the rod 314 may have a variety of dimensions. For instance, in some embodiments, the first end 316 of the rod 314 may have a first dimension (e.g., an outer diameter) between 6 to 20 millimeters, such as about 9 millimeters. In addition, the first end 316 of the rod 314 may have a variety of shapes, such as circular, ovular, square, a square with rounded corners, rectangular, rectangular with rounded corners, triangular, and the like.

In some embodiments, the first end 316 of the rod 314 may support the structure 330 via an interference fit between the structure 330 and the first end 316 of the rod 314. Moreover, in some embodiments, the first end 316 of the rod 314 may include an alignment feature (not shown), and the first end 316 of the rod 314 may support the structure 330 via aligning the structure 330 with the alignment feature of the first end 316 of the rod 314.

Further, the plunger 318 could take various different forms in various different embodiments. For instance, in some embodiments, the plunger 318 may include a complaint material. As examples, the plunger 318 may include a polymer material, such as a silicone elastomer, polyetherimide, PET, polypropylene, and polyurethane.

Moreover, the plunger 318 may have a variety of dimensions. For instance, in some embodiments, the plunger 318 may take the form of a ring with a first dimension (e.g., an inner diameter) that is greater than the outer diameter of the first end 316 of the rod 314, and a second dimension (e.g., an outer diameter) that is less than or substantially the same as a corresponding dimension of the housing 320. And in at least one such embodiment, the outer diameter of the plunger 318 may be greater than 17 millimeters.

The term "substantially the same," as used in this disclosure, refers to exactly the same or one or more deviations from exactly the same that do not significantly impact positioning, by an apparatus, a structure on a polymer layer as described herein.

Further still, the housing 320 could take various different forms in various different embodiments. For instance, in some embodiments, the housing 320 may include a variety of materials, such as a metal (e.g., aluminum and stainless steel) and a rigid plastic. Moreover, the housing 320 may have a variety of dimensions. For instance, in some embodiments, the housing 320 may have a first dimension (e.g., a length) of about 93 millimeters.

Moreover, the spring 322 could take various different forms in various different embodiments. For instance, in some embodiments, the spring 322 could include a variety of materials, such as metal and a polymer. Further, in some such embodiments, the metal may include steel music wire, spring-tempered steel, and/or stainless steel. And, in some such embodiments, the polymer may include an elastomer, polyetherimide, polyether-ether ketone, and/or acetal. For instance, the spring 322 may be Ultem® sold by SABIC. In addition, in some embodiments, the spring 322 may be a compression spring.

1. Placing the Structure at the First End of the Rod

As mentioned above, at block 202, the structure may be placed at the first end of the rod. FIG. 3c illustrates an example in which the fabrication device 300 places the structure 330 at the first end 316 of the rod 314. Further, FIG. 3c-2 illustrates the structure 330.

As shown in FIG. 3c-2, the structure 330 may be a ring-shaped substrate that has an outer diameter and a hole 332 that defines an inner diameter. And the structure 330 may include a polymer 334, a sensor 336, and electronics 338. In an example, the polymer 334 may include a variety of polymeric materials, such as paralyene. Other components could be present in addition to and/or instead of the one or more components of the structure 330 depicted in FIG. 3c-2, as this arrangement is presented by way of example. For instance, in some examples, the structure 330 may further include a battery that may be configured to provide electrical power to the electronics 338.

Figure 4:
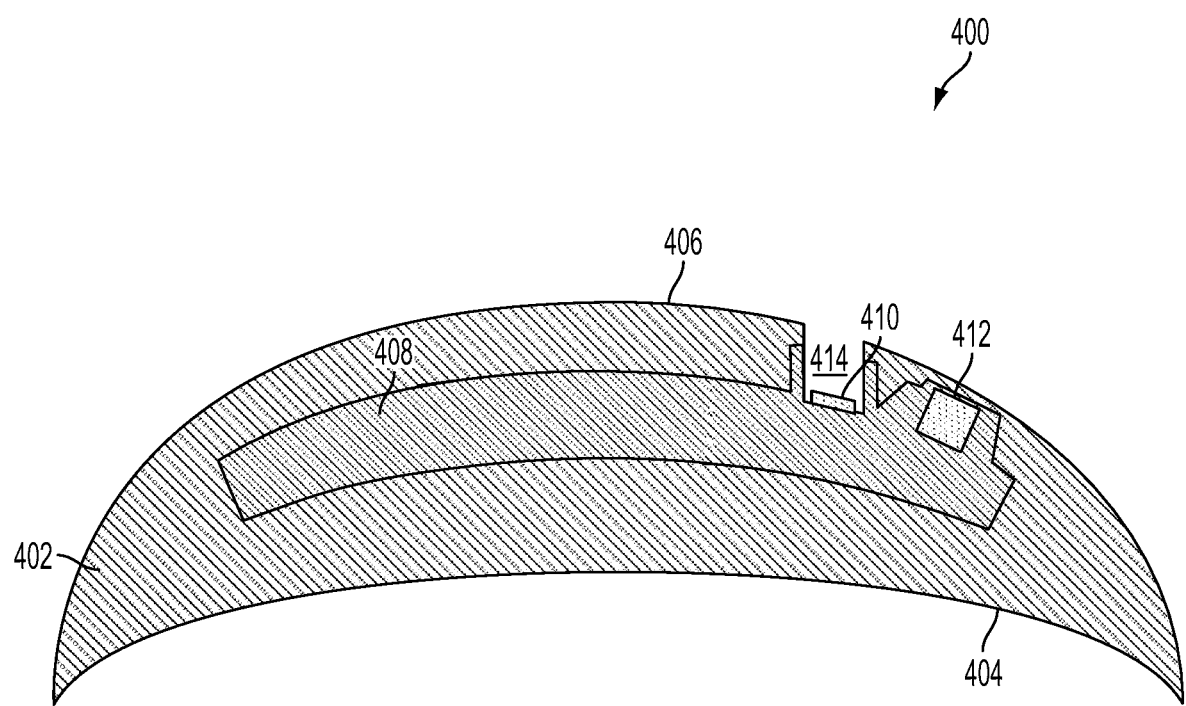
FIG. 4 is an illustration of an eye-mountable device fabricated according to an example embodiment.

The structure 330 may occupy a peripheral portion of an eye-mountable device, such as a fabricated eye-mountable device 400 illustrated in FIG. 4, so as to limit interference with a user's vision when the eye-mountable device is mounted on an eye of the user.

In the illustrated example, the electronics 338 is embedded in the polymer 334, and the sensor 336 is surrounded by the polymer 334, except for the sensor 336 being exposed by an opening 340. However, in other examples, the sensor 336 and electronics 338 may be mounted on a surface of the polymer 334, such as a first surface 342 of the polymer 334 and/or a second surface 344 of the polymer 334 that is opposite the first surface 342. With this arrangement, the structure 330 might not include the opening 340. In some embodiments, the opening 340 can have a dimension of between 500 to 700 micrometers. Other dimensions are possible as well. And, in some embodiments, the opening 340 can have a square shape with rounded corners. Other shapes are possible as well, such as rectangular, circular, etc.

The structure 330 can have various sizes. For instance, the size of the structure 330 may depend on which analyte (or analytes) an eye-mountable device is configured to detect. In an example, the structure 330 is a substrate shaped as a ring with an outer diameter of approximately a 1 centimeter, a radial thickness of approximately 1 millimeter, and a maximum height of approximately 50 between 150 micrometers. Other sizes of the structure 330 are possible as well.

In an example, the structure 330 has a height dimension of at least 50 micrometers. In other words, at some point of the structure 330, the height of the structure 330 may be at least 50 micrometers. In such an example, this height dimension may correspond to a maximum height of the structure 330. In accordance with this disclosure, the maximum height of the structure 330 corresponds to the height of the structure 330 at its highest point. For instance, in the example where the structure 330 includes the sensor 336 and the electronics 338, the height of the structure 330 may vary (and thus the structure 330 may have various height dimensions). For example, the height of the structure 330 may be higher at a point where the electronics 338 is mounted on the structure 330, whereas the height may be lower at a point where the electronics 338 is not mounted on the structure 330. In such an example, the maximum height may correspond to the point where the electronics 338 is located on the structure 330. Further, in an example, the structure 330 can be more rigid than the first polymer layer 308.

The sensor 336 can be configured in a variety of ways. As one example, the sensor 336 may comprise a pair of electrodes, such as a working electrode and a reference electrode, configured to detect one or more analytes. Other configurations of the sensor 336 are possible as well. And the sensor 336 can have a variety of thicknesses. As one example, the sensor 336 can have a thickness of 260 nanometers. Other thicknesses of the sensor 336 are possible as well.

In addition, the electronics 338 can be configured in a variety of ways. As one example, the electronics 338 can comprise a chip including one or more logic elements configured to operate the sensor 336. Other configurations of the electronics 338 are possible as well.

Moreover, in some examples, the structure 330 can include a plurality of loops spaced apart from each other, such as three loops, five loops, nine loops, etc. The loops could include conductive portions encapsulated in a polymer material, for example, to provide an antenna in the structure 330. With such an arrangement, the polymer material may extend between adjacent conductive loops in the plurality of conductive loops during subsequent formation steps.

The structure 330 may be placed at the first end 316 of the rod 314 in a variety of ways. As one example, the fabrication device 300 may further include a positioning system (not shown), such as a robotic system, configured to place the structure 330 at the first end 316 of the rod 314. For instance, the positioning system may (i) pick up the structure 330 (e.g., via suction), (ii) orient the structure 330 above the first end 316 of the rod 314, and then (iii) lower the structure 330 toward the first end 316 of the rod 314. The positioning system may further include a vision system configured to assist with placing the structure 330 at the first end 316 of the rod 314. Such a vision system may facilitate guiding the structure 330 to a precise location at the first end 316 of the rod 314.

Moreover, in order to place the structure 330 at the first end 316 of the rod 314, the positioning system may drive the structure 330 onto the first end 316 of the rod 314. In an example, driving the structure 330 onto the first end 316 of the rod 314 may involve applying a force and/or a torque to the structure 330.

The first end 316 of the rod 314 may support the structure 330 via an interference fit between the structure 330 and the first end 316 of the rod 314. With this arrangement, the structure 330 may conform to the first end of the rod. For example, an outer diameter of the first end 316 of the rod 314 may be greater than an inner diameter of the structure 330. And in some such examples, the outer diameter of the first end 316 of the rod 314 may be 5 micrometers greater than the inner diameter of the structure 330.

Further, as noted, the first end 316 of the rod 314 may include an alignment feature, and the first end 316 of the rod 314 may support the structure 330 via aligning the structure 330 with the alignment feature of the first end 316 of the rod 314. With this arrangement, the structure 330 may be concentrically aligned with the first end 316 of the rod 314. For example, the structure 330 may have an asymmetric diameter and the alignment feature of the first end 316 of the rod 314 may include an asymmetric peg such that the structure 330 receives the alignment feature. The asymmetric peg can be a variety of shapes, such as a star-shaped cross section and a cross-shaped cross section.

The apparatus 312 may be oriented in a variety of ways during the placing of the structure 330 at the first end 316 of the rod 314. For instance, as shown in FIG. 3c, the apparatus 312 is oriented in a direction that is substantially parallel to an axis 346 during the placing of the structure 330 at the first end 316 of the rod 314.

The term "substantially parallel," as used in this disclosure, refers to exactly parallel or one or more deviations from exactly parallel that do not significantly impact positioning, by an apparatus, a structure on a polymer layer as described herein.

Further, in the illustrated example, when the apparatus 312 is oriented in the direction that is substantially parallel to the axis 346, a surface 348 of the first end 316 of the rod 314 may face that direction. With this arrangement, the fabrication device 300 may drive the structure 330 onto the first end 316 of the rod 314 in a direction that is substantially opposite to the axis 346 during the placing of the structure 330 at the first end 316 of the rod 314.

The term "substantially opposite," as used in this disclosure, refers to exactly opposite or one or more deviations from exactly opposite that do not significantly impact positioning, by an apparatus, a structure on a polymer layer as described herein.

However, in other examples, the apparatus 312 may be oriented in a direction that is 180 degrees from the direction that is substantially parallel to the axis 346. With this arrangement, the surface 348 of the first end 316 of the rod 314 may face away from that direction, and the fabrication device 300 may drive the structure 330 onto the first end 316 in a direction that is substantially parallel to the axis 346 during the placing of the structure at the first end 316 of the rod 314.

Further still, in other examples, the apparatus 312 may be oriented in a direction that is at an angle to the axis 346, such as a perpendicular angle or a non-perpendicular angle. Moreover, in at least one such example, the surface 348 of the first end 316 of the rod 314 may face that direction, and the fabrication device 300 may drive the structure 330 onto the first end 316 of the rod 314 in a direction that is substantially parallel to the direction that is at the angle to the axis 346. Alternatively, the surface 348 of the first end 316 of the rod 314 may face away from that direction, and the fabrication device 300 may drive the structure 330 onto the first end 316 of the rod 314 in a direction that is substantially opposite the direction that is at the angle to the axis 346.

In addition, in the illustrated example, the structure 330 is placed at the first end 316 of the rod 314, such that at least a portion of the first surface 342 of the polymer 334 contacts the plunger 318. However, in other examples, the structure 330 may be placed at the first end 316 of the rod 314, such that at least a portion of the second surface 344 of the polymer 334 contacts the plunger 318.

2. Orienting the Apparatus over the First Polymer Layer

As mentioned above, at block 204, the apparatus may be oriented over the first polymer layer. FIG. 3d illustrates an example in which the fabrication device 300 orients the apparatus 312 over the first polymer layer 308.

As shown in FIG. 3d, the apparatus 312 supports the structure 330 as the apparatus 312 is oriented over the first polymer layer 308. With this arrangement, the orienting of the apparatus 312 over the first polymer layer 308 may position a portion of the structure 330 directly above a predetermined location on the first polymer layer 308.

The apparatus 312 may be oriented over the first polymer layer 308 in a variety of ways. As one example, the positioning system described with reference to block 202 may be further configured to orient the apparatus 312 over the first polymer layer 308. With this arrangement, the positioning system may position a portion of the structure 330 directly above a predetermined location on the first polymer layer 308.

In addition, the positioning system may include a vision system that is configured to assist with orienting the apparatus 312 over the first polymer layer 308. For example, the vision system may facilitate guiding the apparatus 312 to a precise location over the first polymer layer 308.

Further, the apparatus 312 may be oriented over the first polymer layer 308 when the surface 348 of the first end 316 of the rod 314 is located a distance 350 over the first polymer layer. With this arrangement, a portion of the structure 330 may be positioned directly above a predetermined location on the first polymer layer 308. The distance 350 could be, for example, between 1 and 100 millimeters. Other values of the distance 350 may be possible as well.

As shown in FIG. 3d, fabrication device 300 may further include an assembly 352 that may support the first polymer layer 308 as the structure is positioned on the first polymer layer 308. With this arrangement, orienting the apparatus 312 over the first polymer layer 308 may involve orienting the apparatus 312 over the assembly 352.

The assembly 352 may include a first plate 354 and a second plate 356 connected to the first plate 354. In the illustrated example, the first plate 354 includes a well 358 where the first polymer layer 308 is located, and the second plate 356 includes a hole 360 that is configured to receive the apparatus 312. With this arrangement, orienting the apparatus 312 over the assembly 352 may involve orienting the apparatus 312 over the hole 360.

In addition, in the illustrated example, the first plate 354 may be connected to the second plate 356 via a first connector 362A and a second connector 362B. The first connector 362A and the second connector 362B may each be connected to the first plate 354 and the second plate 356 in a variety of ways. As one example, first connector 362A may be connected to the first plate 354 and the second plate 356 by one or more welded connections. Similarly, the second connector 362B may be connected to the first plate 354 and the second plate 356 by one or more welded connections. Other techniques for connecting the first connector 362A and the second connector 362B to the first plate 602 and the second plate 604 are possible as well.

The first plate 354, the second plate 356, the first connector 362A, and the second connector 362B may each include a variety of materials, such as a metal (e.g., stainless steel) or a rigid plastic. In an example, the first plate 354, the second plate 356, the first connector 362A, and/or the second connector 362B may be the same material as the housing 320.

In order to orient the apparatus 312 over the first polymer layer 308, the fabrication device 300 may separate the first molding piece 302 from the second molding piece 304. When the fabrication device 300 separates the first molding piece 302 from the second molding piece 304, the first polymer layer 308 may stick to a side of the first molding piece 302. In an example, the first polymer layer 308 and/or the first molding piece 302 can be surface treated, such that the first polymer layer 308 sticks to the side of the first molding piece 302. Additionally or alternatively, the second molding piece 304 can be surface treated, such that the first polymer layer 308 sticks to the side of the first molding piece 302.

In addition, when the fabrication device 300 includes the assembly 352, the fabrication device 300 may (i) remove the first polymer layer 308 from the first molding piece 302 and (ii) place the first polymer layer 308 on the well 358 of the assembly 352, such that the posterior side 310 contacts the well 358. In an example, removing the first polymer layer 308 from the first molding piece 302 can include the fabrication device removing the surface treatment of the first polymer layer 308 and/or the first molding piece 302.

Moreover, in an example, the positioning system may be further configured to place the first polymer layer 308 on the well 358 of the first plate 354. The positioning system may (i) pick up the first polymer layer 308, (ii) orient the first polymer layer 308 over the well 358 of the first plate, and then (iii) lower the first polymer layer 308 toward the well 360 of the first plate 356.

3. Bringing the Apparatus and the First Polymer Layer Together

As mentioned above, at block 206, the apparatus and the first polymer layer may be brought together. FIG. 3e illustrates an example in which the fabrication device 300 brings the apparatus 312 and the first polymer layer 308 together, such that the first end 316 of the rod 314 contacts the first polymer layer 308. In the illustrated example, when the apparatus 312 and the first polymer layer 308 are brought together, at least a portion of the surface 348 of the first end 316 of the rod 314 contacts a surface of the side 311 of the first polymer layer 308. However, in other examples, when the apparatus 312 and the first polymer layer 308 are brought together, some or all of the surface 348 of the first end 316 of the rod 314 and some or all of the second surface 344 of the structure 330 may each contact the surface of the side 311 of the first polymer layer 308.

The apparatus 312 and the first polymer layer 308 may be brought together in a variety of ways. As one example, the positioning system may be further configured to bring the apparatus 312 and the first polymer layer 308 together. In addition, the vision system of the positioning system may be further configured to assist with bringing the apparatus 312 and the first polymer layer 308 together.

As noted, the hole 360 of the second plate 356 is configured to receive the apparatus 312. With this arrangement, bringing the apparatus 312 and the first polymer layer 308 together may involve bringing a portion of the apparatus 312 through the hole 360 of the second plate 356.

In addition, bringing the apparatus 312 and the first polymer layer 308 together may involve bringing the apparatus 312 toward the first polymer 308 in a predetermined direction. In the illustrated example, the apparatus 312 is brought toward the first polymer layer 308 in a direction that is substantially parallel to an axis 364. However, in other examples, the apparatus 312 may be brought towards the first polymer layer 308 in a direction that is at an angle to the axis 364, such as a non-perpendicular angle.

4. Driving the Apparatus into a Transfer Position

As mentioned above, at block 208, the apparatus may be driven into the transfer position. FIG. 3f illustrates an example in which the fabrication device 300 drives the apparatus 312 into the transfer position. In the illustrated example, the apparatus 312 is driven in a direction that is substantially parallel to the axis 364.

As shown in FIG. 3f, in the transfer position (i) the plunger 318 presses the structure 330 onto the first polymer layer 308 and (ii) the rod 314 retracts into the housing 320. In some examples, the rod 314 may retract into the housing 320 in response to a movement of the plunger 318 during the driving of the apparatus 312 into the transfer position.

Moreover, as shown in FIG. 3f, the spring 322 may deform a certain distance 366 when the rod 314 retracts into the housing 320. As examples, the certain distance 366 may be between 2 to 15 millimeters. Moreover, in some examples, the certain distance 366 may be a sagittal depth of the first polymer layer 308, which could be, for example, between 6 to 7 millimeters. The deformation of the spring 322 could involve either compression or expansion of the spring 322 over the certain distance 366.

Further, in the illustrated example, when the plunger 318 presses the structure 330 onto the first polymer layer 308, the plunger 318 may conform to a curvature of the structure 330. And in the illustrated example, when the plunger 318 presses the structure onto the first polymer layer 308, the apparatus 312 may bend the structure 330 to conform to a curvature of the side 311 of the first polymer layer 308.

The apparatus 312 may be driven into the transfer position in a variety of ways. As one example, the positioning apparatus may be further configured to drive the apparatus 312 into the transfer position by applying a force and/or a torque to the apparatus 312. For instance, in some embodiments, driving the apparatus 312 into the transfer position may involve applying a force to the flange 328 of the housing 320. In an example, the applied force may involve placing one or more weights on the flange 328. The one or more weights may take the form of or be similar in form to one or more washers, such as five washers. And in some such examples, the one or more weights may weigh between 170 to 425 grams.

As noted above, in an example, the first polymer layer 308 in a partially-cured state may have a tackiness that facilitates adhesion thereto. With this arrangement, the structure 330 may remain adhered to the first polymer layer 308 in a secure location during subsequent formation steps.

After the apparatus 312 is driven into the transfer position, the structure 330 is positioned on the first polymer layer 308. With this arrangement, the sensor 336 may be mounted at a particular angle along a circumference of the first polymer layer 308. As a result, the sensor 336 may be placed at a precise location in an XYZ plane on the first polymer layer 308. As one example, the sensor 336 may rest a 6 o'clock position on the first polymer layer 308. As another example, the sensor 336 may rest at a 12 o'clock position on the first polymer layer 308.

5. Applying an Adhesive to the Structure, and in the Transfer Position, Curing the Adhesive The method 200 may further involve applying an adhesive to the structure 330, and in the transfer position, curing the adhesive. In some examples, applying the adhesive to the structure 330 may occur before placing the structure 330 at the first end 316 of the rod 314. However, in other examples, applying the adhesive to the structure 330 may occur after placing the structure 330 at the first end 316 of the rod 314. In some such examples, applying the adhesive to the structure 330 may occur before bringing the apparatus 312 and the first polymer layer 308 together.

The adhesive could be applied to the structure 330 in a variety of ways. For instance, the fabrication device 300 may apply (e.g., spray, paint, stamp, and the like) the adhesive onto a surface of the structure 330 that contacts the first polymer layer 308, such as the second surface 344 or the first surface 342. With this arrangement, the adhesive may facilitate adhesion of the structure 330 to the first polymer layer 308. In addition, the adhesive could take various different forms in various different embodiments. As one example, the adhesive may include a silicone resin. In addition, the adhesive may include any of the materials that the first polymer layer 308 and/or second polymer layer 376 may include. Other types of adhesives are possible as well.

Moreover, in some embodiments, in the transfer position, curing the adhesive may be performed after the apparatus 312 is driven into the transfer position. With this arrangement, the plunger 318 may press the structure 330 onto the first polymer layer 308 as the adhesive is being cured. As examples, the adhesive may be cured thermally, or by ultraviolet or visible light.

6. Bending the Structure

The method 200 may further involve bending the structure 330. In some examples, bending the structure 330 may occur before placing the structure 330 at the first end 316 of the rod 314.

The structure 330 may be bent in a variety of ways. For instance, the positioning system may be further configured to bend the structure 330. With this arrangement, positioning the structure 330 onto the first polymer layer 308 may be improved. For instance, bending the structure 330 before placing the structure 330 at the first end 316 of the rod 314 may reduce bending of the structure 330 by the apparatus 312 during positioning of the structure 330 on the first polymer 308.

The positioning system may bend the structure 330 by applying a force and/or a torque to one or more portions of the structure 330. As one example, the structure 330 may be bent to a curvature of a side of the first polymer layer, such as the side 311.

Although method 200 was described above with the fabrication device 300 including the assembly 352, in other examples the fabrication device 300 might not include the assembly 352. Instead, a molding piece, such as the first molding piece 302, may support the first polymer layer 308 as the structure 330 is being positioned on the first polymer layer 308.

Figure 3G:
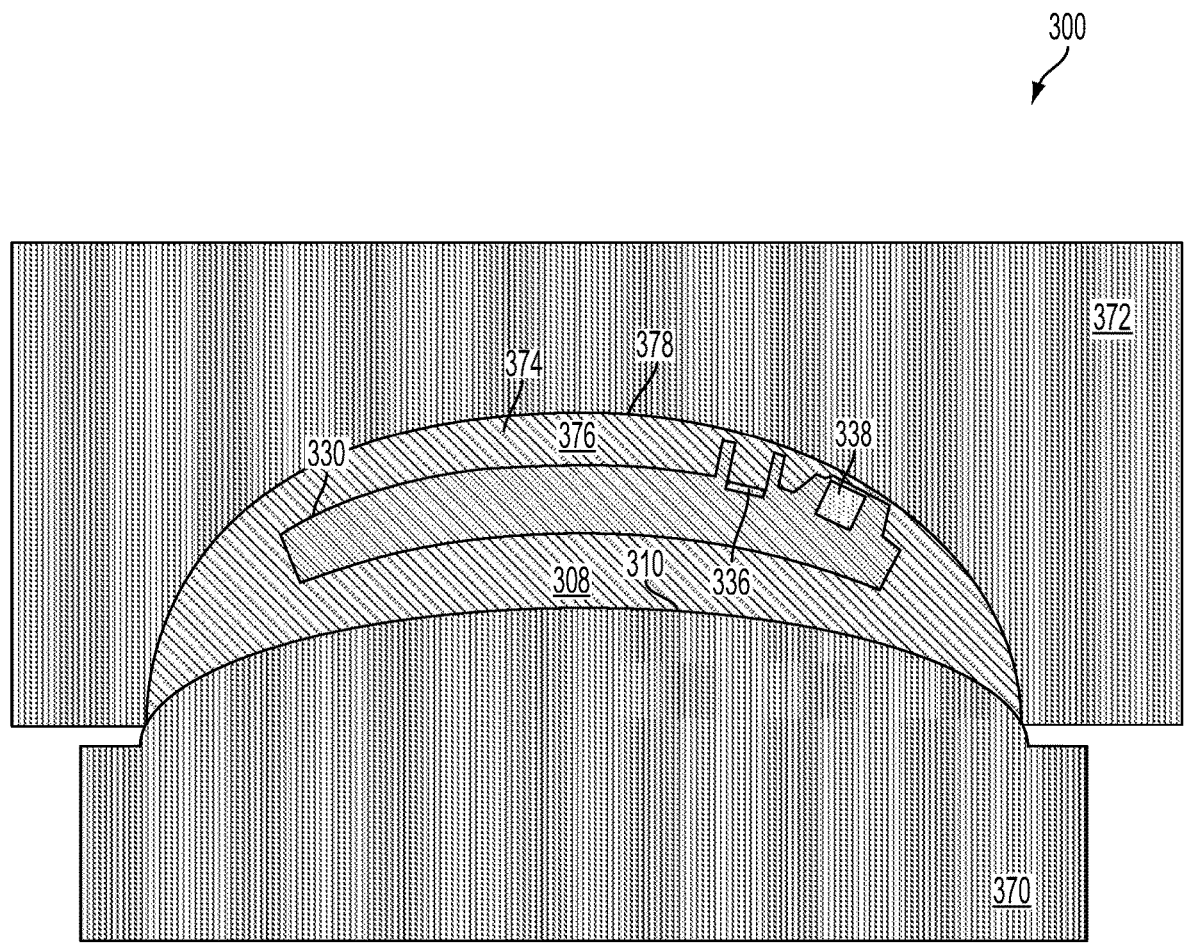
FIG. 3g is an illustration of formation of a second polymer layer, according to an example embodiment.

C. Forming a Second Polymer Layer over the First Polymer Layer and the Structure As mentioned above, at block 106, the fabrication device may form a second polymer layer over the first polymer layer and the structure, such that the structure is fully enclosed by the first polymer layer and the second polymer layer. FIG. 3g illustrates the fabrication device 300 including example molding pieces that may be used to form the second polymer layer. In particular, FIG. 3g illustrates a third molding piece 370 and a fourth molding piece 372. The third molding piece 370 and the fourth molding piece 372 may define a second cavity. In some examples, the first molding piece 302 may be used as the third molding piece 370.

The structure 330 mounted on the first polymer layer 308 may define a partially-fabricated device 368 (as illustrated in FIG. 3f). In order to form the second polymer layer, the partially-fabricated device 368 may be placed on the third molding piece 370. In an example, the positioning system may be further configured to place the partially-fabricated device 368 on the third molding piece 370. The positioning system may (i) pick up the partially-fabricated device 368, (ii) orient the partially-fabricated device 368 above the third molding piece 370, and (iii) lower the partially-fabricated device 368 toward the third molding piece 370. In addition, the vision system of the positioning system may further be configured to assist with placing the partially-fabricated device 368 on the third molding piece 370.

After the partially-fabricated device 368 is placed on the third molding piece 370, the third molding piece 370 may be filled with a polymer material 374. The polymer material 374 may be formed into a second polymer layer 376 by compression between the third molding piece 370 and the fourth molding piece 372. As a result, the second polymer layer 376 may mold over the structure 330, such that the structure 330 is fully enclosed by the first polymer layer 308 and the second polymer layer 376.

After the second polymer layer 376 is formed, the fabrication device 300 may cure the second polymer layer 376. In an example, the second polymer layer 376 can be cured like the first polymer layer 308. However, in other examples, the second polymer layer 376 may be cured by different techniques than the first polymer layer 308. The second polymer layer 376 can be cured by any of the techniques mentioned herein. In an example, the fabrication device 300 may cure the first polymer layer 308 at this stage.

After the second polymer layer 376 is cured, there may not be a visible boundary line separating the first polymer layer 308 from the second polymer layer 376. For example, FIG. 4 illustrates the fabricated eye-mountable device 400. In particular, FIG. 4 illustrates the eye-mountable device 400 includes a transparent polymer 402. The transparent polymer 402 can be arranged like the first polymer layer 308 and the second polymer layer 376.

Returning to FIG. 3g, the fabrication device 300 may further comprise one or more alignment pins (not shown), such as a plurality of dowel pins, for aligning the fourth molding piece 372 and the third molding piece 370. The one or more alignment pins can assist in forming the second polymer layer 376 by aligning the fourth molding piece 372 with the first molding piece 370.

The third molding piece 370 and the fourth molding piece 372 may be configured to achieve a given desired thickness of a layer formed between the two pieces. As one example, the third molding piece 370 and the fourth molding piece 372 may be designed so as to define a thickness of the second polymer layer 376. As another example, the third molding piece 370 and the fourth molding piece 372 may be designed so as to define a final thickness of an eye-mountable device, such as the eye-mountable device 400. In an example, the third molding piece 370 and the fourth molding piece 372 can be designed so as to allow for a layer having a given desired thickness between the two pieces (in addition to a thickness of the first polymer 308). As such, when the third molding piece 370 and the fourth molding piece 372 are pressed together during formation of a layer, the resulting layer will have the given desired thickness.

In an example, the second polymer layer 376 has a thickness of greater than 50 micrometers. However, in other examples, the second polymer layer 376 can have a thickness between 50 and 300 micrometers, such as 130 micrometers. It should be understood that since the second polymer layer 376 molds over the structure 330, the second polymer layer 376 may not have a uniform thickness. For instance, the thickness of the second polymer layer 376 above the sensor 336 may be less than the thickness of the second polymer layer 376 that is not touching the sensor 336.

In an example, the thickness of the second polymer layer 376 can be selected based on a particular analyte or analytes that the eye-mountable device, such as the eye-mountable device 400, is configured to detect. For example, an optimal thickness for a first analyte may be 10 micrometers, while an optimal thickness for a second analyte may be 25 micrometers. Other examples are possible as well.

In an example, the second polymer layer 376 can be composed of the same polymer material as the first polymer layer 308. However, in other examples, the second polymer layer 376 can be composed of a different polymer material than the first polymer layer 308. The second polymer layer 376 can be any one of the polymer materials mentioned herein. In an example, the structure 330 can be more rigid than the second polymer layer 376.

The second polymer layer 376 defines an anterior side 378 (or second side) of an eye-mountable device. That is, the second polymer layer 376 defines an outer edge of the eye-mountable device. When mounted on an eye of a user, the anterior side 378 of the eye-mountable device defined by the second polymer layer 376 corresponds to the side of the device that is not touching the eye of the user. The fourth molding piece 372 may be shaped so as to define a shape of the anterior side 378. For example, a curvature of the anterior side 378 may be defined by the fourth molding piece 372.

Although the method 100 and the method 200 were described above with respect to the structure 330, in other examples the structure might not include a ring-shaped substrate. Instead, the structure may include an electronic component, such as a light emitting diode (LED). With this arrangement, embodiments described herein may allow for such a structure to be positioned at a predetermined location on the first polymer layer 308, such as at a center of the first polymer layer 308. For instance, the apparatus 312 may be configured to position the structure at the predetermined location on the first polymer layer 308. As one example, the first end 316 of the rod 314 could include a hole configured to receive the structure, such that the first end 316 of the rod 314 supports the structure as the structure is being positioned on the first polymer layer 308, and the plunger 318 could press the structure onto the first polymer layer 308 as the structure is being positioned on the first polymer layer 308.

D. Applying a Non-Stick Coating to the Plunger

The method 100 may further involve applying a non-stick coating to the plunger 318. In some examples, applying the non-stick coating to the plunger 338 may occur before positioning the structure 330 on the first polymer layer 308, such as before placing the structure 330 at the first end 316 of the rod 314.

The non-stick coating could be applied in a variety of ways. For instance, the fabrication device 330 may apply (e.g., spray, paint, stamp, and the like) the non-stick coating to the plunger 318. With this arrangement, the plunger 318 may not stick (or bond) to the first polymer layer 308 and/or the structure 330 during positioning of the structure 330 on the first polymer layer 308. The non-stick coating may take various different forms in various different embodiments. As one example, the non-stick coating may include paralyne. Other non-stick coatings are possible as well.

E. Forming a Channel to the Sensor

The method 100 may further involve forming a channel to the sensor 336, such that the sensor 336 is configured to receive one or more analytes via the channel. The channel could be formed in a variety of ways. As one example, the channel may be formed by removing material from the second polymer layer 376. The material from the second polymer layer 376 may be removed to form the channel in a variety of ways. For instance, the material from the second polymer layer 376 may be removed to form the channel via a process that includes drilling, ablation, etching, etc.

As another example, a mask layer may be formed over sensor 336 before forming the second polymer layer 376. With this arrangement, the second polymer layer 376 may mold over the mask layer. In some situations, the mask layer may take the shape of the opening 340. Further, in such an example, the mask layer may be removed to form the channel to the sensor 336. The mask layer may be removed in a variety of ways. For instance, the mask layer may be removed via a process that includes etching the mask layer, dissolving the mask layer in a fluid, and/or soaking the mask layer in a fluid.

As still another example, the channel may be molded. For instance, the second polymer layer 376 may be formed in a molding piece that includes a protrusion that extends from a surface of the molding piece to the sensor 336 through the second polymer layer 376 as the second polymer layer 376 is being formed. With this arrangement, the protrusion may form the channel to the sensor 336.

As mentioned above, FIG. 4 illustrates the eye-mountable device 400 formed according to an example embodiment. In the eye-mountable device 400, a structure 408 is embedded in the transparent polymer 402. In some examples, the structure 408 may be embedded in the transparent polymer 402 in a predetermined orientation, such as centered in the transparent polymer 402.

The structure 408 includes a sensor 410 configured to detect an analyte and electronics 412. The eye-mountable device 400 includes a posterior side 404 and an anterior side 406. The transparent polymer 402 may take the form of or be similar in form to the first polymer layer 308 and the second polymer layer 376, the structure 408 may take the form of or be similar in form to the structure 330, the sensor 410 may take the form of or be similar in form to the sensor 336, and the electronics 412 may take the form of or be similar in form to the electronics 338.

In an example, the sensor 314 may be configured to receive the analyte via a channel 414 in the transparent polymer 402. With this arrangement, the structure 408 is fully enclosed by the transparent polymer 402, except for the sensor 414 being exposed by the channel 414.

In some examples, one or more dimensions of the channel 414 may be based on one or more dimensions of the sensor 410 and/or the electronics 412. As one example, a width of the channel 414 can be based on a width of the sensor 410. As another example, a height of the channel 414 can be based on a height of the electronics 412.

While the body-mountable device has been described as comprising the eye-mountable device 400, the body-mountable device could comprise other mountable devices that are mounted on or in other portions of the human body.

For example, in some embodiments, the body-mountable device may comprise a tooth-mountable device. In some embodiments, the tooth-mountable device may take the form of or be similar in form to the eye-mountable device 400. For instance, the tooth-mountable device may include polymer layers and/or a transparent polymer that are the same or similar to any of the polymer layers and/or transparent polymers described herein and a structure that is the same or similar to any of the structures described herein. With this arrangement, the tooth-mountable device may be configured to detect at least one analyte in a fluid (e.g., saliva) of a user wearing the tooth-mountable device.

Moreover, in some embodiments, the body-mountable device may comprise a skin-mountable device. In some embodiments, the skin-mountable device may take the form of or be similar in form to the eye-mountable device 400. For instance, the tooth-mountable device may include polymer layers and/or a transparent polymer that are the same or similar to any of the polymer layers and/or transparent polymers described herein and a structure that is the same or similar to any of the structures described herein. With this arrangement, the skin-mountable device may be configured to detect at least one analyte in a fluid (e.g., perspiration, blood, etc.) of a user wearing the skin-mountable device.

Further, some embodiments may include privacy controls which may be automatically implemented or controlled by the wearer of a body-mountable device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a body-mountable device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

III. Example Apparatus, Systems, and Devices

A. Example Apparatus

As mentioned above, a body-mountable device may be formed using example methods described above. Apparatus for placing a structure on a polymer layer is described in greater detail below with reference to FIGS. 5 and 6. It is noted that relative dimensions in FIGS. 5 and 6 are not necessarily to scale, but have been rendered for purposes of explanation only in describing the arrangement of the apparatus.

The structure positioned on the polymer layer by the apparatus described herein may take the form of or be similar in form to the structure 330. And the polymer layer may take the form of or be similar in form to the first polymer layer 308.

Figure 5:
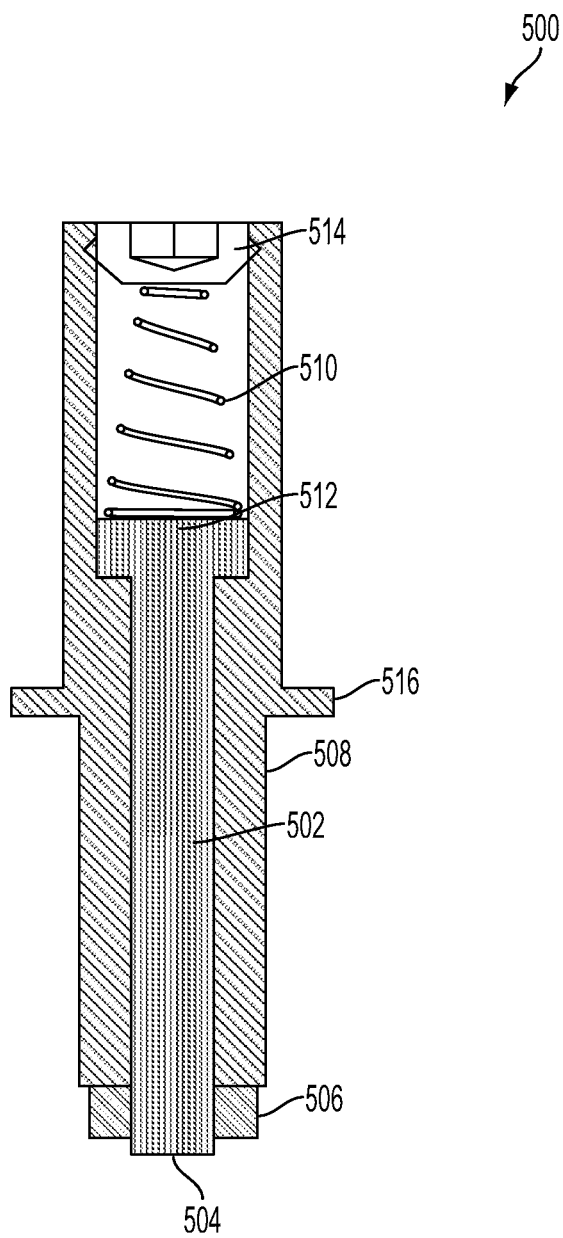
FIG. 5 is an illustration of an apparatus for placing a structure on a polymer layer, according to an example embodiment.
Figure 6:
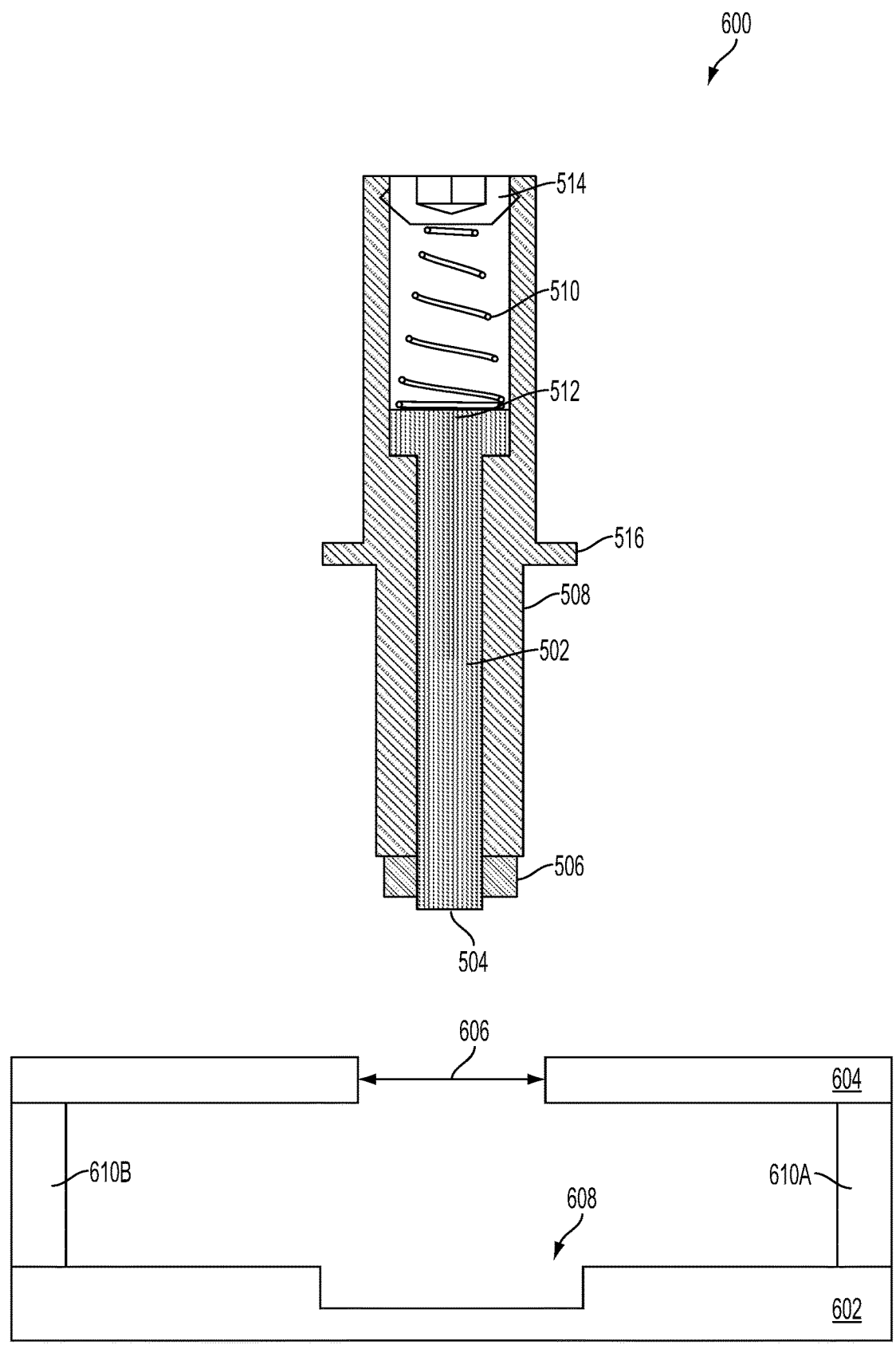
FIG. 6 is an illustration of another apparatus for placing a structure on a polymer layer, according to an example embodiment.

FIG. 5 illustrates an apparatus 500 for positioning a structure on a polymer layer, according to an example embodiment. As shown in FIG. 5, the apparatus 500 includes a rod 502 having a first end 504 that is configured to support the structure as the structure is being positioned on the polymer layer and a plunger 506 located around the first end 504 of the rod 502, where the plunger 506 is configured to press the structure onto the polymer layer as the structure is being positioned on the polymer layer.

The rod 502 may take the form of or be similar in form to the rod 314, the first end 504 of the rod 502 may take the form of or be similar in form to the first end 316 of the rod 314, and the plunger 506 may take the form of or be similar in form to the plunger 318.

For instance, in some embodiments, at least one of the rod or plunger may include a complaint material, such as a polymer material. Moreover, in some embodiments, the first end 504 of the rod 502 may be configured to support the structure via an interference between the structure at the first end 504 of the rod 502. Further, in some embodiments, the first end 504 of the rod 502 may include an alignment feature, and the first end 504 of the rod 502 may be configured to support the structure via alignment of the structure with the alignment feature of the first end 504 or the rod 502.

In an example, the apparatus 500 may further include a housing 508 and a spring 510, and the rod 502 may further include a second end 512. The spring 510 may be connected to the second end 512 of the rod 502 and may be configured to retract the rod 502 into the housing 508 during positioning of the structure. In addition, the spring 510 may be connected to the housing 508 via a set screw 514.

The housing 508 may take the form of or be similar in form to the housing 320, the spring 510 may take the form of or be similar in form to the spring 322, the second end 512 of the rod 502 may take the form of or be similar in form to the second end 324 of the rod 314, and the set screw 514 may take the form of or be similar in form to the set screw 326.

In another example, the housing 508 may include a flange 516 that may be configured to receive a force to drive the housing 508 into a transfer position, where in the transfer position (i) the plunger 506 presses the structure onto the polymer layer and (ii) the rod 502 retracts into the housing 508. In some examples, the rod 502 may retract into the housing 508 in response to a movement of the plunger 506 during the driving of the housing 508 into the transfer position. The flange 516 may take the form of or be similar in form to the flange 328.

FIG. 6 illustrates another apparatus 600 for placing a structure on a polymer layer. In particular, the apparatus 600 includes a first plate 602 and a second plate 604 connected to the first plate 602.

In addition, the apparatus 600 includes the rod 502, the plunger 506, the housing 508, and the spring 510. The rod 502 includes the first end 504 and the second end 512. The first end 504 of the rod 502 is configured to support the structure as the structure is being positioned on the polymer layer. And the plunger 508 is located around the first end 504 of the rod 502, and the plunger 508 is configured to press the structure onto the polymer layer as the structure is being positioned.

In apparatus 600, the spring 510 may be connected to the second end 512 of the rod 502 and may be configured to retract the rod 502 into the housing 508 during positioning of the structure. In addition, the spring 510 may be connected to the housing 508 via the set screw 514.

Further, in the apparatus 600, the housing 508 may include a flange 516 that is configured to receive a force to drive the housing 508 into a transfer position, where in the transfer position (i) the plunger 506 presses the structure onto the polymer layer and (ii) the rod 502 retracts into the housing 508. In some examples, the rod 502 may retract into the housing 508 in response to a movement of the plunger 506 during the driving of the housing 508 into the transfer position.

As noted, the apparatus 600 includes the first plate 602 and the second plate 604 connected to the first plate 602. The first plate 602 may be configured to support the polymer layer as the structure is being positioned on the polymer layer. And the second plate 604 may be configured to support the housing 508 as the structure is being positioned on the polymer layer. The first plate 602 may take the form of or be similar in form to the first plate 354, and the second plate 604 may take the form of or be similar in form to the second plate 356.

In an example, the second plate 604 may include a hole 606, and the second plate 604 may be configured to support the housing 508 by receiving the housing 508 through the hole 606. For instance, the second plate 604 may be configured to support the housing 508 when (i) the first end 504 of the rod 502 contacts the polymer layer and (ii) when the housing 508 is driven into the transfer position. The hole 606 may take the form of or be similar in form to the hole 360.

In another example, the first plate 602 may include a well 608, and the first plate 602 may be configured to support the polymer layer by receiving the polymer layer in the well 608. The well 608 may take the form of or be similar in form to the well 358.

In still another example, the apparatus 600 may further include a first connector 610A and a second connector 610B, and the first plate 602 may be connected to the second plate 604 via the first connector 610A and the second connector 610B. The first connector 610A may take the form of or be similar in form to the first connector 362A, and the second connector 610B may take the form of or be similar in form to the second connector 362B.

Although apparatus 500 and apparatus 600 were described above with the structure taking the form of or being similar in form to the structure 330, in other examples the structure might not include a ring-shaped substrate. Instead, the structure may include an electronic component, such as a LED. With this arrangement, apparatus 500 and apparatus 600 may each be configured to position the structure at a predetermined location on the polymer layer, such as at a center of the polymer layer. As one example, the first end 504 of the rod 502 could include a hole configured to receive the structure, and the plunger 506 could be configured to press the structure onto the polymer layer.

B. Example System and Devices

As mentioned above, a body-mountable device may be formed using the example methods described above. Further, the body-mountable device may be configured to monitor health-related information based on at least one analyte detected in a fluid of a user wearing the body-mountable device. An eye-mountable device configured to monitor health-related information based on at least one analyte detected from an eye of a user is described in greater detail below with reference to FIGS. 7 and 8a-8d.

A structure in accordance with an example embodiment may include a sensor, electronics, and an antenna all situated on a substrate. The electronics may operate the sensor to perform readings and operate the antenna to wirelessly communicate the readings from the sensor to an external reader via the antenna. The sensor can be arranged on the substrate to face outward, away from the corneal surface of the user, so as to generate clinically relevant readings from tear fluid of the user that the sensor receives via a channel in the anterior side of the eye-mountable device. For example, the sensor can be suspended in the lens material and situated such that the sensor is less than 10 micrometers from the anterior edge of the eye-mountable device. The sensor can generate an output signal indicative of a concentration of an analyte that the sensor receives via the channel.

Figure 7:
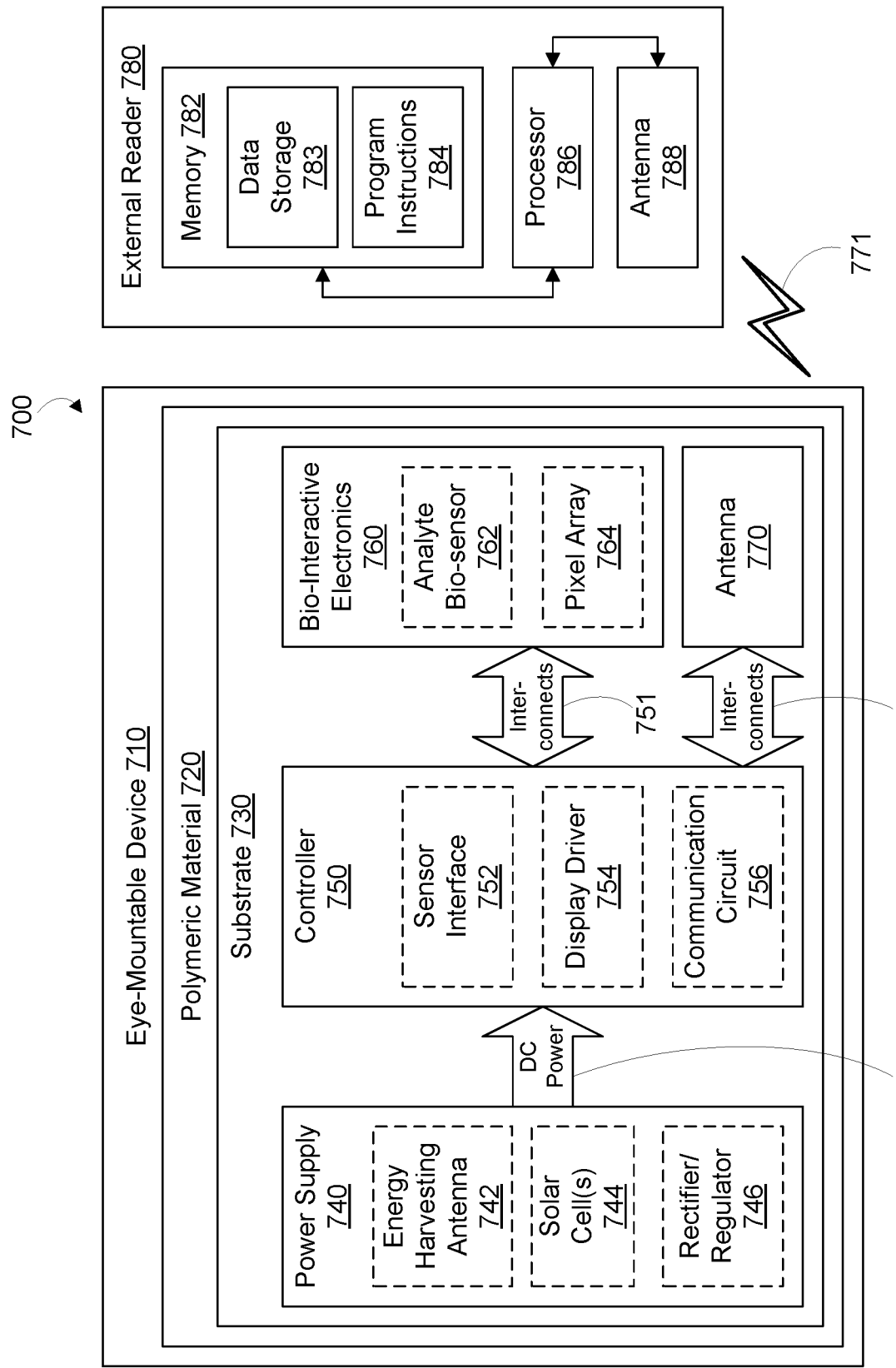
FIG. 7 is a block diagram of a system with an eye-mountable device in wireless communication with an external reader, according to an example embodiment.

FIG. 7 is a block diagram of a system 700 with an eye-mountable device 710 in wireless communication with an external reader 780. The exposed regions of the eye-mountable device 710 are made of a polymeric material 720 formed to be contact-mounted to a corneal surface of an eye. In accordance with the exemplary methods, polymeric material 720 may comprise a first polymer layer and a second polymer layer.

Substrate 730 is embedded in the polymeric material 720 to provide a mounting surface for a power supply 740, a controller 750, bio-interactive electronics 760, and an antenna 770. The bio-interactive electronics 760 are operated by the controller 750. The power supply 740 supplies operating voltages to the controller 750 and/or the bio-interactive electronics 760. The antenna 770 is operated by the controller 750 to communicate information to and/or from the eye-mountable device 710. The antenna 770, the controller 750, the power supply 740, and the bio-interactive electronics 760 can all be situated on the embedded substrate 730. Because the eye-mountable device 710 includes electronics and is configured to be contact-mounted to an eye, it may also be referred to as an ophthalmic electronics platform.

To facilitate contact-mounting, the polymeric material 720 can have a concave surface configured to adhere ("mount") to a moistened corneal surface (e.g., by capillary forces with a tear film coating the corneal surface). Additionally or alternatively, the eye-mountable device 710 can be adhered by a vacuum force between the corneal surface and the polymeric material due to the concave curvature. While mounted with the concave surface against the eye, the anterior or outward-facing surface of the polymeric material 720 can have a convex curvature that is formed to not interfere with eye-lid motion while the eye-mountable device 710 is mounted to the eye. For example, the polymeric material 720 can be a substantially transparent curved polymeric disk shaped similarly to a contact lens.

The polymeric material 720 can include one or more biocompatible materials, such as those employed for use in contact lenses or other ophthalmic applications involving direct contact with the corneal surface. The polymeric material 720 can optionally be formed in part from such biocompatible materials or can include an outer coating with such biocompatible materials. The polymeric material 720 can include materials configured to moisturize the corneal surface, such as hydrogels and the like. In some instances, the polymeric material 720 can be a deformable ("non-rigid") material to enhance wearer comfort. In some instances, the polymeric material 720 can be shaped to provide a predetermined, vision-correcting optical power, such as can be provided by a contact lens.

The substrate 730 includes one or more surfaces suitable for mounting the bio-interactive electronics 760, the controller 750, the power supply 740, and the antenna 770. The substrate 730 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) can be patterned on the substrate 730 to form circuitry, electrodes, etc. For example, the antenna 770 can be formed by depositing a pattern of gold or another conductive material on the substrate 730. Similarly, interconnects 751, 757 between the controller 750 and the bio-interactive electronics 760, and between the controller 750 and the antenna 770, respectively, can be formed by depositing suitable patterns of conductive materials on the substrate 730. A combination of resists, masks, and deposition techniques can be employed to pattern materials on the substrate 730.

The substrate 730 can be a relatively rigid polymeric material, such as PET, paralyene or another material sufficient to structurally support the circuitry and/or electronics within the polymeric material 720. The eye-mountable device 710 can alternatively be arranged with a group of unconnected substrates rather than a single substrate. For example, the controller 750 and a bio-sensor or other bio-interactive electronic component can be mounted to one substrate, while the antenna 770 is mounted to another substrate and the two can be electrically connected via the interconnects 757.

In some embodiments, the bio-interactive electronics 760 (and the substrate 730) can be positioned away from the center of the eye-mountable device 710 and thereby avoid interference with light transmission to the eye through the center of the eye-mountable device 710. For example, where the eye-mountable device 710 is shaped as a concave-curved disk, the substrate 730 can be embedded around the periphery (e.g., near the outer circumference) of the disk. In some embodiments, the bio-interactive electronics 760 (and the substrate 730) can be positioned in the center region of the eye-mountable device 710. The bio-interactive electronics 760 and/or the substrate 730 can be substantially transparent to incoming visible light to mitigate interference with light transmission to the eye. Moreover, in some embodiments, the bio-interactive electronics 760 can include a pixel array 764 that emits and/or transmits light to be perceived by the eye according to display driver instructions. Thus, the bio-interactive electronics 760 can optionally be positioned in the center of the eye-mountable device so as to generate perceivable visual cues to a wearer of the eye-mountable device 710, such as by displaying information via the pixel array 764.

The substrate 730 can be shaped as a flattened ring with a radial width dimension sufficient to provide a mounting platform for the embedded electronics components. The substrate 730 can have a thickness sufficiently small to allow the substrate 730 to be embedded in the polymeric material 720 without influencing the profile of the eye-mountable device 710. The substrate 730 can have a thickness sufficiently large to provide structural stability suitable for supporting the electronics mounted thereon. For example, the substrate 730 can be shaped as a ring with a diameter of about 10 millimeters, a radial width of about 1 millimeter (e.g., an outer radius 1 millimeter larger than an inner radius), and a thickness of about 50 micrometers. The substrate 730 can optionally be aligned with the curvature of the anterior side of the eye-mountable device.

The power supply 740 is configured to harvest ambient energy to power the controller 750 and bio-interactive electronics 760. For example, a radio-frequency energy harvesting antenna 742 can capture energy from incident radio radiation. Additionally or alternatively, solar cell(s) 744 ("photovoltaic cells") can capture energy from incoming ultraviolet, visible, and/or infrared radiation. Furthermore, an inertial power scavenging system can be included to capture energy from ambient vibrations. The energy harvesting antenna 742 can optionally be a dual-purpose antenna that is also used to communicate information to the external reader 780. That is, the functions of the antenna 770 and the energy harvesting antenna 742 can be accomplished with the same physical antenna.

A rectifier/regulator 746 can be used to condition the captured energy to a stable DC supply voltage 741 that is supplied to the controller 750. For example, the energy harvesting antenna 742 can receive incident radio frequency radiation. Varying electrical signals on the leads of the antenna 742 are output to the rectifier/regulator 746. The rectifier/regulator 746 rectifies the varying electrical signals to a DC voltage and regulates the rectified DC voltage to a level suitable for operating the controller 750. Additionally or alternatively, output voltage from the solar cell(s) 744 can be regulated to a level suitable for operating the controller 750. The rectifier/regulator 746 can include one or more energy storage devices arranged to mitigate high frequency variations in the ambient energy harvesting antenna 742 and/or solar cell(s) 744. For example, an energy storage device (e.g., capacitor, inductor, etc.) can be connected to the output of the rectifier/regulator 746 so as to function as a low-pass filter.

The controller 750 is turned on when the DC supply voltage 741 is provided to the controller 750, and the logic in the controller 750 operates the bio-interactive electronics 760 and the antenna 770. The controller 750 can include logic circuitry configured to operate the bio-interactive electronics 760 so as to interact with a biological environment of the eye-mountable device 710. The interaction could involve the use of one or more components, such as an analyte bio-sensor 762, in bio-interactive electronics 760 to obtain input from the biological environment. Alternatively or additionally, the interaction could involve the use of one or more components, such as the pixel array 764, to provide an output to the biological environment.

In one example, a sensor interface module 752 can be included for operating the analyte bio-sensor 762. The analyte bio-sensor 762 can be, for example, an amperometric electrochemical sensor that includes a working electrode and a reference electrode. Application of an appropriate voltage between the working and reference electrodes can cause an analyte to undergo electrochemical reactions (e.g., reduction and/or oxidation reactions) at the working electrode to generate an amperometric current. The amperometric current can be dependent on the analyte concentration, and thus the amount of amperometric current can provide an indication of analyte concentration. In some embodiments, the sensor interface module 752 can be a potentiostat configured to apply a voltage difference between the working and reference electrodes while measuring a current through the working electrode.

In some instances, a reagent can also be included to sensitize the electrochemical sensor to desired analytes. For example, a layer of glucose oxidase ("GOX") can be situated around the working electrode to catalyze glucose into hydrogen peroxide ($H_2O_2$). The hydrogen peroxide can then be oxidized at the working electrode, which releases electrons to the working electrode, which generates a current.

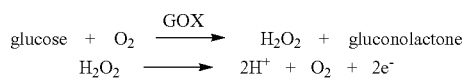

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate can be approximately proportionate to the concentration of the analyte molecules. The current can thus provide an indication of the analyte concentration.

The controller 750 can optionally include a display driver module 754 for operating the pixel array 764. The pixel array 764 can be an array of separately programmable light transmitting, light reflecting, and/or light emitting pixels arranged in rows and columns. The individual pixel circuits can optionally include liquid crystal technologies, micro-electromechanical technologies, emissive diode technologies, etc. to selectively transmit, reflect, and/or emit light according to information from the display driver module 754. Such a pixel array 764 can also optionally include more than one color of pixels (e.g., red, green, and blue pixels) to render visual content in color. The display driver module 754 can include, for example, one or more data lines providing programming information to the separately programmed pixels in the pixel array 764 and one or more addressing lines for setting groups of pixels to receive such programming information. Such a pixel array 764 situated on the eye can also include one or more lenses to direct light from the pixel array to a focal plane perceivable by the eye.

The controller 750 can also include a communication circuit 756 for sending and/or receiving information via the antenna 770. The communication circuit 756 can optionally include one or more oscillators, mixers, frequency injectors, etc. to modulate and/or demodulate information on a carrier frequency to be transmitted and/or received by the antenna 770. In some examples, the eye-mountable device 710 is configured to indicate an output from a bio-sensor by modulating an impedance of the antenna 770 in a manner that is perceivable by the external reader 780. For example, the communication circuit 756 can cause variations in the amplitude, phase, and/or frequency of backscatter radiation from the antenna 770, and such variations can be detected by the external reader 780.

The controller 750 is connected to the bio-interactive electronics 760 via interconnects 751. For example, where the controller 750 includes logic elements implemented in an integrated circuit to form the sensor interface module 752 and/or display driver module 754, a patterned conductive material (e.g., gold, platinum, palladium, titanium, copper, aluminum, silver, metals, combinations of these, etc.) can connect a terminal on the chip to the bio-interactive electronics 760. Similarly, the controller 750 is connected to the antenna 770 via interconnects 757.

It is noted that the block diagram shown in FIG. 7 is described in connection with functional modules for convenience in description. However, embodiments of the eye-mountable device 710 can be arranged with one or more of the functional modules ("sub-systems") implemented in a single chip, integrated circuit, and/or physical feature. For example, while the rectifier/regulator 746 is illustrated in the power supply block 740, the rectifier/regulator 746 can be implemented in a chip that also includes the logic elements of the controller 750 and/or other features of the embedded electronics in the eye-mountable device 710. Thus, the DC supply voltage 741 that is provided to the controller 750 from the power supply 740 can be a supply voltage that is provided on a chip by rectifier and/or regulator components of the same chip. That is, the functional blocks in FIG. 7 shown as the power supply block 740 and controller block 750 need not be implemented as separated modules. Moreover, one or more of the functional modules described in FIG. 7 can be implemented by separately packaged chips electrically connected to one another.

Additionally or alternatively, the energy harvesting antenna 742 and the antenna 770 can be implemented with the same physical antenna. For example, a loop antenna can both harvest incident radiation for power generation and communicate information via backscatter radiation.

The external reader 780 includes an antenna 788 (or group of more than one antennae) to send and receive wireless signals 771 to and from the eye-mountable device 710. The external reader 780 also includes a computing system with a processor 786 in communication with a memory 782. The memory 782 is a non-transitory computer-readable medium that can include, without limitation, magnetic disks, optical disks, organic memory, and/or any other volatile (e.g., RAM) or non-volatile (e.g., ROM) storage system readable by the processor 786. The memory 782 can include a data storage 783 to store indications of data structures, such as sensor readings (e.g., from the analyte bio-sensor 762), program settings (e.g., to adjust behavior of the eye-mountable device 710 and/or external reader 780), etc. The memory can also include program instructions 784 for execution by the processor 786 to cause the external reader to perform processes specified by the program instructions 784. For example, the program instructions 784 can cause external reader 780 to provide a user interface that allows for retrieving information communicated from the eye-mountable device 710 (e.g., sensor outputs from the analyte bio-sensor 762). The external reader 780 can also include one or more hardware components for operating the antenna 788 to send and receive the wireless signals 771 to and from the eye-mountable device 710. For example, oscillators, frequency injectors, encoders, decoders, amplifiers, filters, etc. can drive the antenna 788 according to instructions from the processor 786.

The external reader 780 can be a smart phone, digital assistant, or other portable computing device with wireless connectivity sufficient to provide the wireless communication link 771. The external reader 780 can also be implemented as an antenna module that can be plugged in to a portable computing device, such as in an example where the communication link 771 operates at carrier frequencies not commonly employed in portable computing devices. In some instances, the external reader 780 is a special-purpose device configured to be worn relatively near a wearer's eye to allow the wireless communication link 771 to operate with a low power budget. For example, the external reader 780 can be integrated in eyeglasses, integrated in a piece of jewelry such as a necklace, earring, etc., or integrated in an article of clothing worn near the head, such as a hat, headband, etc.

In an example where the eye-mountable device 710 includes an analyte bio-sensor 762, the system 700 can be operated to monitor the analyte concentration in tear film on the surface of the eye. Thus, the eye-mountable device 710 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 700 configured as a tear film analyte monitor, the external reader 780 can emit radio frequency radiation 771 that is harvested to power the eye-mountable device 710 via the power supply 740. Radio frequency electrical signals captured by the energy harvesting antenna 742 (and/or the antenna 770) are rectified and/or regulated in the rectifier/regulator 746 and a regulated DC supply voltage 741 is provided to the controller 750. The radio frequency radiation 771 thus turns on the electronic components within the eye-mountable device 710. Once turned on, the controller 750 operates the analyte bio-sensor 762 to measure an analyte concentration level. For example, the sensor interface module 752 can apply a voltage between a working electrode and a reference electrode in the analyte bio-sensor 762 sufficient to cause the analyte to undergo an electrochemical reaction at the working electrode. The current through the working electrode can be measured to provide the sensor output indicative of the analyte concentration. The controller 750 can operate the antenna 770 to communicate the sensor results back to the external reader 780 (e.g., via the communication circuit 756). The sensor result can be communicated by, for example, modulating an impedance of the antenna 770 such that the modulation in impedance is detected by the external reader 780. The modulation in antenna impedance can be detected by, for example, backscatter radiation from the antenna 770.

In some embodiments, the system 700 can operate to non-continuously ("intermittently") supply energy to the eye-mountable device 710 to power the on-board controller 750 and electronics 760. For example, radio frequency radiation 771 can be supplied to power the eye-mountable device 710 long enough to carry out a tear film analyte concentration measurement and communicate the results. For example, the supplied radio frequency radiation can provide sufficient power to charge two electrodes to a potential sufficient to induce electrochemical reactions, measure the resulting amperometric current, and modulate the antenna impedance to adjust the backscatter radiation in a manner indicative of the measured current. In such an example, the supplied radio frequency radiation 771 can be considered an interrogation signal from the external reader 780 to the eye-mountable device 710 to request a measurement. By periodically interrogating the eye-mountable device 710 (e.g., by supplying radio frequency radiation 771 to temporarily turn the device on) and storing the sensor results (e.g., via the data storage 783), the external reader 780 can accumulate a set of analyte concentration measurements over time without continuously powering the eye-mountable device 710.

Figure 8A:
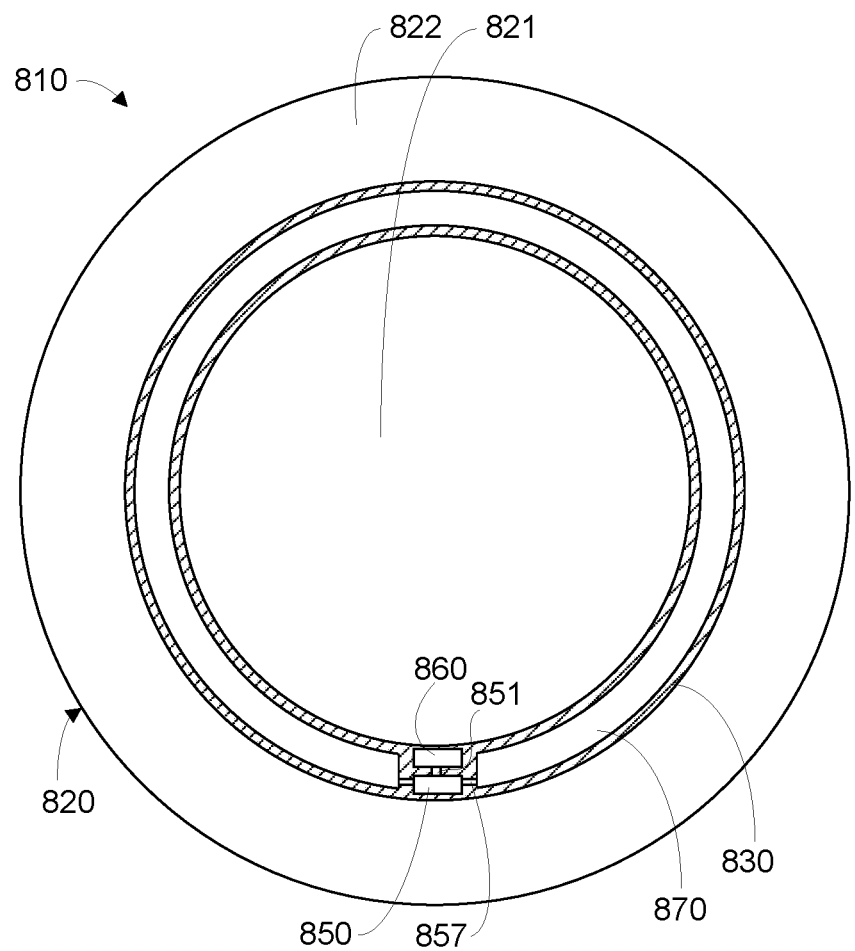
FIG. 8a is a top view of an eye-mountable device, according to an example embodiment.
Figure 8B:
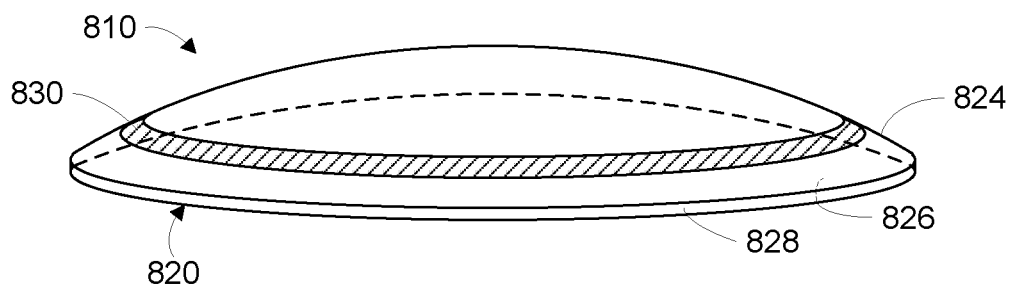
FIG. 8b is a side view of an eye-mountable device, according to an example embodiment.

FIG. 8a is a top view of an eye-mountable electronic device 810. FIG. 8b is a side view of the eye-mountable electronic device shown in FIG. 8a. It is noted that relative dimensions in FIGS. 8a and 8b are not necessarily to scale, but have been rendered for purposes of explanation only in describing the arrangement of the eye-mountable electronic device 810. The eye-mountable device 810 is formed of a polymeric material 820 shaped as a curved disk. The polymeric material 820 can be a substantially transparent material to allow incident light to be transmitted to the eye while the eye-mountable device 810 is mounted to the eye. The polymeric material 820 can be a biocompatible material similar to those employed to form vision correction and/or cosmetic contact lenses in optometry, such as PET, polymethyl methacrylate ("PMMA"), silicone hydrogels, combinations of these, etc. The polymeric material 820 can be formed with one side having a concave surface 826 suitable to fit over a corneal surface of an eye. The opposing side of the disk can have a convex surface 824 that does not interfere with eyelid motion while the eye-mountable device 810 is mounted to the eye. A circular outer side edge 828 connects the concave surface 826 and convex surface 824.

The eye-mountable device 810 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 810 can be selected according to the size and/or shape of the corneal surface and/or the scleral surface of the wearer's eye.

While the eye-mountable device 810 is mounted in an eye, the convex surface 824 (i.e., the anterior surface) faces outward to the ambient environment while the concave surface 826 (i.e., the posterior surface) faces inward, toward the corneal surface. The convex surface 824 can therefore be considered an outer, top surface of the eye-mountable device 810 whereas the concave surface 826 can be considered an inner, bottom surface. The "top" view shown in FIG. 8*a* is facing the convex surface 824.

A substrate 830 is embedded in the polymeric material 820. The substrate 830 can be embedded to be situated along the outer periphery 822 of the polymeric material 820, away from the center region 821. The substrate 830 does not interfere with vision because it is too close to the eye to be in focus and is positioned away from the center region 821 where incident light is transmitted to the light-sensing portions of the eye. Moreover, the substrate 830 can be formed of a transparent material to further mitigate any effects on visual perception.

The substrate 830 can be shaped as a flat, circular ring (e.g., a disk with a central hole). The flat surface of the substrate 830 (e.g., along the radial width) is a platform for mounting electronics such as chips (e.g., via flip-chip mounting) and for patterning conductive materials (e.g., via deposition techniques) to form electrodes, antenna(e), and/or connections. The substrate 830 and the polymeric material 820 can be approximately cylindrically symmetric about a common central axis. The substrate 830 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only. The substrate 830 can be implemented in a variety of different form factors.

A loop antenna 870, a controller 850, and bio-interactive electronics 860 are disposed on the embedded substrate 830. The controller 850 can be a chip including logic elements configured to operate the bio-interactive electronics 860 and the loop antenna 870. The controller 850 is electrically connected to the loop antenna 870 by interconnects 857 also situated on the substrate 830. Similarly, the controller 850 is electrically connected to the bio-interactive electronics 860 by interconnects 851. The interconnects 851, 857, the loop antenna 870, and any conductive electrodes (e.g., for an electrochemical analyte bio-sensor, etc.) can be formed from conductive materials patterned on the substrate 830 by a process for precisely patterning such materials, such as deposition or lithography. The conductive materials patterned on the substrate 830 can be, for example, gold, platinum, palladium, titanium, carbon, aluminum, copper, silver, silver-chloride, and/or other materials.

Figure 8D:
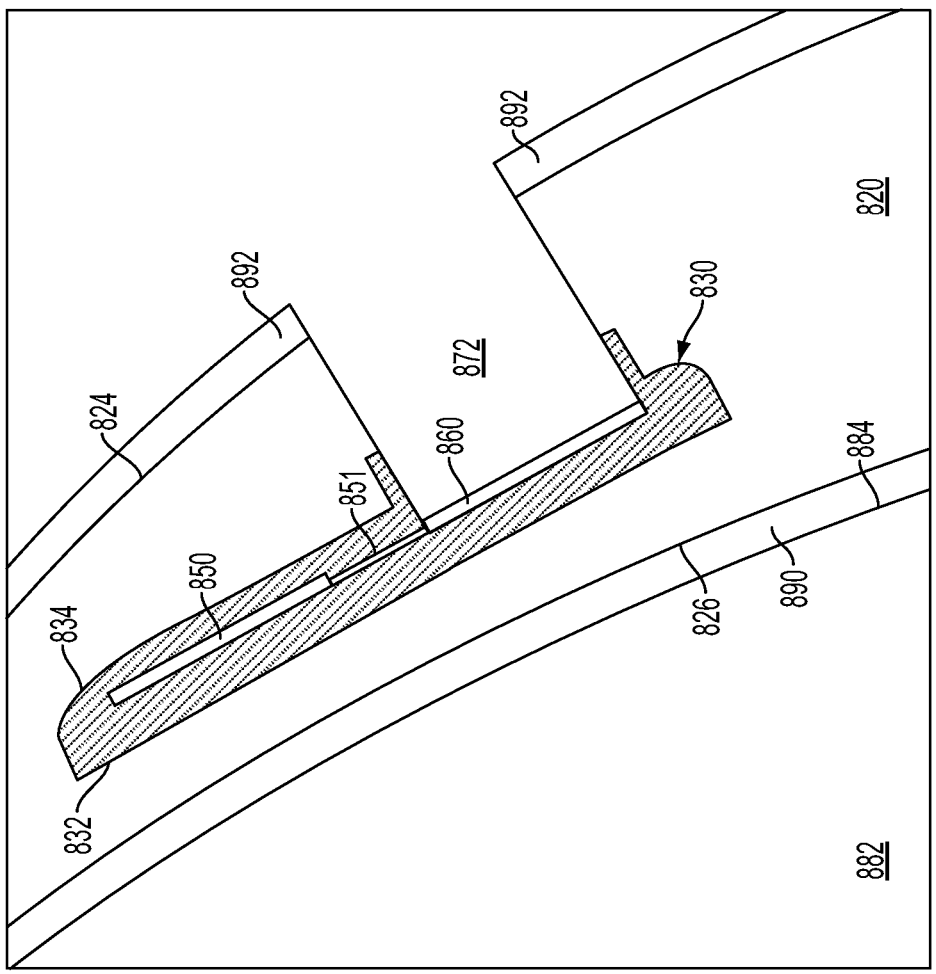
FIG. 8d is a side cross-section view showing the tear film layers surrounding the surfaces of the eye-mountable device mounted as shown in FIG. 8c, according to an example embodiment.
Figure 8C:
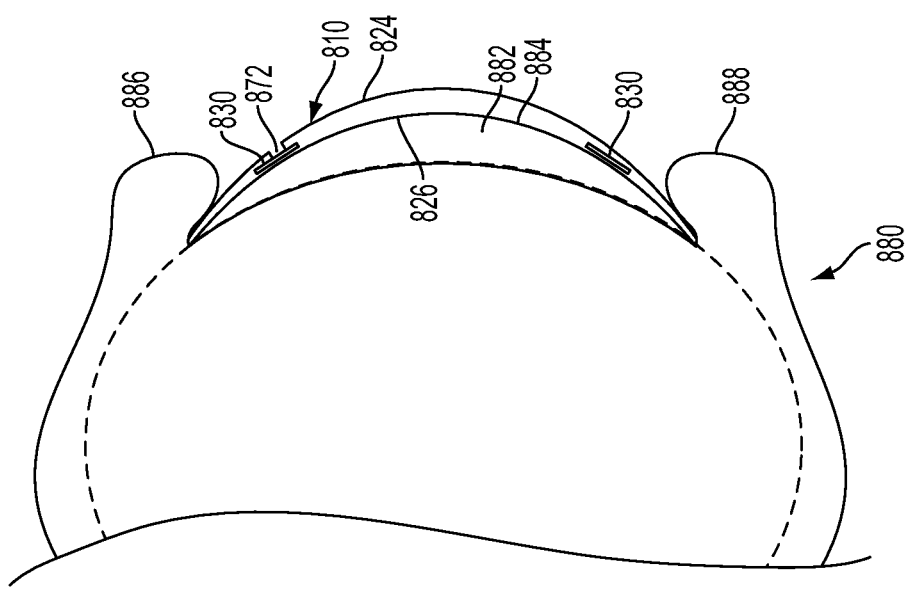
FIG. 8c is a side cross-section view of the eye-mountable device of FIGS. 8a and 8b while mounted to a corneal surface of an eye, according to an example embodiment.

With reference to FIG. 8*a*, which is a view facing the convex surface 824 of the eye-mountable device 810, the bio-interactive electronics 860 is mounted to a side of the substrate 830 facing the convex surface 824. Where the bio-interactive electronics 860 includes an analyte bio-sensor, for example, mounting such a bio-sensor on the substrate 830 facing the convex surface 824 allows the bio-sensor to receive analyte concentrations in tear film through a channel 872 in the polymeric material 820 to the convex surface 824 (as illustrated in FIGS. 8*c* and 8*d*). In some embodiments, some electronic components can be mounted on one side of the substrate 830, while other electronic components are mounted to the opposing side, and connections between the two can be made through conductive materials passing through the substrate 830.

The loop antenna 870 is a layer of conductive material patterned along the flat surface of the substrate to form a flat conductive ring. In some instances, the loop antenna 870 can be formed without making a complete loop. For instance, the loop antenna 870 can have a cutout to allow room for the controller 850 and the bio-interactive electronics 860, as illustrated in FIG. 8*a*. However, the loop antenna 870 can also be arranged as a continuous strip of conductive material that wraps entirely around the flat surface of the substrate 830 one or more times. For example, a strip of conductive material with multiple windings can be patterned on the side of the substrate 830 opposite the controller 850 and bio-interactive electronics 860. Interconnects between the ends of such a wound antenna (e.g., the antenna leads) can be passed through the substrate 830 to the controller 850. In some embodiments, the loop antenna can include a plurality of conductive loops spaced apart from each other, such as three conductive loops, five conductive loops, nine conductive loops, etc. With such an arrangement, the polymeric material 820 may extend between adjacent conductive loops in the plurality of conductive loops.

FIG. 8*c* is a side cross-section view of the eye-mountable electronic device 810 while mounted to a corneal surface 884 of an eye 880. FIG. 8*d* is a close-in side cross-section view enhanced to show tear film layers 890, 892 surrounding the exposed surfaces 824, 826 of the eye-mountable device 810. It is noted that relative dimensions in FIGS. 8*c* and 8*d* are not necessarily to scale, but have been rendered for purposes of explanation only in describing the arrangement of the eye-mountable electronic device 810. For example, the total thickness of the eye-mountable device 810 can be about 200 micrometers, while the thickness of the tear film layers 890, 892 can each be about 10 micrometers, although this ratio may not be reflected in the drawings. Some aspects are exaggerated to allow for illustration and facilitate explanation.

The eye 880 includes a cornea 882 that is covered by bringing the upper eyelid 886 and lower eyelid 888 together over the top of the eye 880. Incident light is received by the eye 880 through the cornea 882, where light is optically directed to light sensing elements of the eye 880 (e.g., rods and cones, etc.) to stimulate visual perception. The motion of the eyelids 886, 888 distributes a tear film across the exposed corneal surface 884 of the eye 880. The tear film is an aqueous solution secreted by the lacrimal gland to protect and lubricate the eye 880. When the eye-mountable device 810 is mounted in the eye 880, the tear film coats both the convex and concave surfaces 824, 826 with an inner layer 890 (along the concave surface 826) and an outer layer 892 (along the convex surface 824). The tear film layers 890, 892 can be about 10 micrometers in thickness and together account for about 10 microliters.

The tear film layers 890, 892 are distributed across the corneal surface 884 and/or the convex surface 824 by motion of the eyelids 886, 888. For example, the eyelids 886, 888 raise and lower, respectively, to spread a small volume of tear film across the corneal surface 884 and/or the convex surface 824 of the eye-mountable device 810. The tear film layer 890 on the corneal surface 884 also facilitates mounting the eye-mountable device 810 by capillary forces between the concave surface 826 and the corneal surface 884. In some embodiments, the eye-mountable device 810 can also be held over the eye in part by vacuum forces against the corneal surface 884 due to the concave curvature of the eye-facing concave surface 826.

As shown in the cross-sectional views in FIGS. 8c and 8d, the substrate 830 can be inclined such that the flat mounting surfaces of the substrate 830 are approximately parallel to the adjacent portion of the convex surface 824. As described above, the substrate 830 is a flattened ring with an inward-facing surface 832 (facing the concave surface 826 of the polymeric material 820) and an outward-facing surface 834 (facing the convex surface 824). The substrate 830 can have electronic components and/or patterned conductive materials mounted to either or both mounting surfaces 832, 834.

As shown in FIG. 8d, the bio-interactive electronics 860, the controller 850, and the conductive interconnect 851 are located between the outward-facing surface 834 and the inward-facing surface 832 such that the bio-interactive electronics 860 are facing the convex surface 824. As described above, the polymer layer defining the anterior side may be greater than 50 micrometers thick, whereas the polymer layer defining the posterior side may be less than 150 micrometers. Thus, the bio-interactive electronics 860 may be at least 50 micrometers away from the convex surface 824 and may be a greater distance away from the concave surface 826. However, in other examples, the bio-interactive electronics 860 may be mounted on the inward-facing surface 832 of the substrate 830 such that the bio-interactive electronics 860 are facing the concave surface 826. The bio-interactive electronics 860 could also be positioned closer to the concave surface 826 than the convex surface 824. With this arrangement, the bio-interactive electronics 860 can receive analyte concentrations in the tear film 892 through the channel 872.

While the body-mountable device has been described as comprising the eye-mountable device 710 and/or the eye-mountable device 810, the body-mountable device could comprise other mountable devices that are mounted on or in other portions of the body.

As noted, in some embodiments, the body-mountable device may comprise a tooth-mountable device. In some embodiments, the tooth-mountable device may take the form of or be similar in form to the eye-mountable device 710 and/or the eye-mountable device 810. For instance, the tooth-mountable device may include a polymeric material that is the same or similar to any of the polymeric materials described herein and a substrate that is the same or similar to any of the substrates described herein.

As noted, in some embodiments, the body-mountable device may comprise a skin-mountable device. In some embodiments, the skin-mountable device may take the form of or be similar in form to the eye-mountable device 710 and/or the eye-mountable device 810. For instance, the skin-mountable device may include a polymeric material that is the same or similar to any of the polymeric materials described herein and a substrate that is the same or similar to any of the substrates described herein.

IV. Conclusion

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

What is claimed is:

1. An apparatus for placing a structure on a polymer layer, the apparatus comprising:
   a rod having a first end and a second end, wherein the first end of the rod supports the structure as the structure is being positioned on the polymer layer via an interference fit between the structure and the first end of the rod;

a plunger located around the first end of the rod, wherein the plunger presses the structure onto the polymer layer as the structure is being positioned on the polymer layer;

a housing having a flange; and a spring connected to the second end of the rod, wherein the spring retracts into the housing during positioning of the structure, wherein the flange receives a force to drive the housing into a transfer position, and wherein in the transfer position: (i) the plunger presses the structure onto the polymer layer and (ii) the rod retracts into the housing.

2. The apparatus of claim 1, wherein the plunger is coaxially located around the first end of the rod.

3. The apparatus of claim 1, wherein the first end of the rod comprises a non-stick coating.

4. An apparatus for placing a structure on a polymer layer, the apparatus comprising:

a rod having a first end and a second end, wherein the first end of the rod supports the structure as the structure is being positioned on the polymer layer;

a plunger located around the first end of the rod, wherein the plunger presses the structure onto the polymer layer as the structure is being positioned on the polymer layer;

a housing having a flange; and a spring connected to the second end of the rod, wherein the spring retracts the rod into the housing during positioning of the structure, and wherein the flange receives a force to drive the housing into a transfer position, wherein in the transfer position: (i) the plunger presses the structure onto the polymer layer and (ii) the rod retracts into the housing.

5. The apparatus of claim 4, wherein at least one of the rod or the plunger comprises a polymer material.

6. The apparatus of claim 5, wherein the first end of the rod supports the structure via an interference fit between the structure and the first end of the rod.

7. The apparatus of claim 5, wherein the first end of the rod comprises an alignment feature, and wherein the first end of the rod supports the structure via alignment of the structure with the alignment feature of the first end of the rod.

8. The apparatus of claim 4 further comprising: a first plate and a second plate connected to the first plate, wherein the first plate supports the polymer layer as the structure is being positioned on the polymer layer, wherein the second plate comprises a hole, and wherein the second plate supports the housing as the structure is being positioned on the polymer layer by receiving the housing through the hole.

9. The apparatus of claim 4, wherein the plunger is coaxially located around the first end of the rod.

10. The apparatus of claim 4, wherein the first end of the rod comprises a circular shape, wherein the plunger comprises a ring, and wherein an inner diameter of the plunger is greater than an outer diameter of the first end of the rod.

11. The apparatus of claim 4, wherein the first end of the rod comprises a non-stick coating.

12. The apparatus of claim 4, wherein the structure comprises a ring-shaped substrate.

13. The apparatus of claim 4, wherein the structure comprises an electronic component.

14. An apparatus for placing a structure on a polymer layer, the apparatus comprising:

a rod having a first end and a second end, wherein the first end of the rod comprises an alignment feature, and wherein the first end of the rod supports the structure as the structure is being positioned on the polymer layer via alignment of the structure with the alignment feature of the first end of the rod;

a plunger located around the first end of the rod, wherein the plunger presses the structure onto the polymer layer as the structure is being positioned on the polymer layer;

a housing having a flange; and a spring connected to the second end of the rod, wherein the spring retracts into the housing during positioning of the structure, wherein the flange receives a force to drive the housing into a transfer position, and wherein in the transfer position: (i) the plunger presses the structure onto the polymer layer and (ii) the rod retracts into the housing.

15. The apparatus of claim 14, wherein the first end of the rod comprises a non-stick coating.

* * * * *